United States Patent
Ilan et al.

(10) Patent No.: US 9,387,222 B2
(45) Date of Patent: Jul. 12, 2016

(54) ALGINATE BIOMATERIALS FOR THE TREATMENT OF HEPATIC DISORDERS

(75) Inventors: Yaron Ilan, Jerusalem (IL); Gadi Lalazar, Mevasseret Zion (IL); Eyal Shteyer, Mevasseret Zion (IL); Ami Ben-Yaakov, Jerusalem (IL); Smadar Cohen, Beer Sheva (IL); Tsiona Elkayam, Moshav Taashur (IL)

(73) Assignees: Hadasit Medical Research Services and Development Ltd., Jerusalem (IL); Ben-Gurion University of the Negev Research and Development Authority, Beer-Sheva (IL)

( * ) Notice: Subject to any disclaimer, the term of this patent is extended or adjusted under 35 U.S.C. 154(b) by 0 days.

(21) Appl. No.: 12/744,512

(22) PCT Filed: Nov. 27, 2008

(86) PCT No.: PCT/IL2008/001552
§ 371 (c)(1),
(2), (4) Date: May 25, 2010

(87) PCT Pub. No.: WO2009/069131
PCT Pub. Date: Jun. 4, 2009

(65) Prior Publication Data
US 2010/0247652 A1   Sep. 30, 2010

(30) Foreign Application Priority Data
Nov. 27, 2007   (IL) .......................................... 187707

(51) Int. Cl.
| | |
|---|---|
| *A61K 9/00* | (2006.01) |
| *A61K 9/10* | (2006.01) |
| *A61K 38/02* | (2006.01) |
| *A61P 1/16* | (2006.01) |
| *A61K 31/734* | (2006.01) |
| *A61K 31/738* | (2006.01) |
| *A61L 27/20* | (2006.01) |
| *A61L 31/04* | (2006.01) |

(52) U.S. Cl.
CPC ............ *A61K 31/734* (2013.01); *A61K 31/738* (2013.01); *A61L 27/20* (2013.01); *A61L 31/042* (2013.01)

(58) Field of Classification Search
None
See application file for complete search history.

(56) References Cited

U.S. PATENT DOCUMENTS 5,709,854 A * 1/1998 Griffith-Cima ......... A61L 27/50
   424/426
5,876,742 A * 3/1999 Cochrum et al. ............. 424/424
6,334,968 B1 * 1/2002 Shapiro et al. ................ 264/28
7,642,240 B2   1/2010 Cohen et al.
2007/0081976 A1   4/2007 Cohen et al.

FOREIGN PATENT DOCUMENTS

| DE | 19723155 | 12/1998 |
|---|---|---|
| WO | WO 95/19743 | 7/1995 |
| WO | WO 97/44070 | 11/1997 |
| WO | WO 98/12228 | 3/1998 |
| WO | WO 2004/082594 | 9/2004 |
| WO | WO 2004/098669 | 11/2004 |
| WO | WO 2008/098109 | 8/2008 |
| WO | WO 2009/069131 | 6/2009 |

OTHER PUBLICATIONS

Tristan Turquois and Hugo Gloria. Determination of the Absolute Molecular Weight Averages and Molecular Weight Distributions of Alginates Used as Ice Cream Stabilizers by Using Multiangle Laser Light Scattering Measurements. J. Agric. Food Chem. 2000, 48, 5455-5458.*
Yuri S. Khotimchenko and Maxim Y. Khotimchenko. Healing and Preventive Effects of Calcium Alginate on Carbon Tetrachloride Induced Liver Injury in Rats. Mar. Drugs 2004, 2, 108-122.*
Ikuyo Ichi, Kayoko Nakahara, Kozue Fujii, Chinatsu Iida, Yayoi Miyashita and Shosuke Kojo. Increase of Ceramide in the Liver and Plasma after Carbon Tetrachloride Intoxication in the Rat. J Nutr Sci Vitaminol, 53, 53-56, 2007.*
Biji Balakrishnan and A. Jayakrishnan. Self-cross-linking biopolymers as injectable in situ forming biodegradable scaffolds. Biomaterials 26 (2005) 3941-3951.*
Mona Dvir-Ginzberg, Iris Gamlieli-Bonshtein, Riad Agbaria, Smadar Cohen. Liver Tissue Engineering within Alginate Scaffolds: Effects of Cell-Seeding Density on Hepatocyte Viability, Morphology, and Function. Tissue Engineering, vol. 9, No. 4, 2003, pp. 757-766.*
Douglas B. Seifert and Janice A. Phillips. Production of Small, Monodispersed Alginate Beads for Cell Immobilization. Biotechnol. Prog. 1997, 13, 562-568.*
A. Martinsen, G. Skjak-Braek, and 0. Smidsrod. Alginate as Immobilization Material: I. Correlation between Chemical and Physical Properties of Alginate Gel Beads. Biotechnology and Bioengineering, vol. 33, pp. 79-89 (1989).*
Fact sheet from Sigma Aldrich Chemical Company, downloaded May 30, 2012 from site: http://sigma-aldrich.custhelp.com/app/answers/detail/a_id/2175/p/4,697/session/L3RpbWUvMTMzODQxMTg1Ny9zaWQvcElrbGNyWms%3D.*

(Continued)

*Primary Examiner* — Frederick Krass
*Assistant Examiner* — Michael P Cohen

(57) ABSTRACT

The present invention relates to methods for the treatment of hepatic disorders in a subject in need thereof. More specifically, the methods of the invention are based on the administration, preferably, systemic administration, of a therapeutically effective amount of at least one biocompatible alginate biomaterial, any modification thereof and any combination thereof. The invention further provides methods for sustaining serum albumin levels, and/or reducing serum AST and ALT, in subjects suffering from hepatic disorder. Still further, the invention provides methods for reducing apoptosis and inducing cell proliferation in a damaged liver tissue of a subject suffering of hepatic disorder, using the alginate biomaterial described by the invention.

15 Claims, 14 Drawing Sheets

(56) References Cited

OTHER PUBLICATIONS

H. Maruyama, A. Harada, T. Kurokawa, H. Kobayashi, T. Nonami, A. Nakao, H. Takagi. Duration of Liver Ischemia and Hepatic Regeneration after Hepatectomy in Rats. Journal of Surgical Research, 58, 290-294, 1995.*
Definition of "hepatectomy" from Dictionary.com, downloaded Mar. 5, 2014 from: http://dictionary.reference.com/browse/hepatectomy.*
George Lukas, Shirley D. Brindle, and Paul Greengard. The Journal of Pharmacology and Experimental Therapeutics 1971, 178(3), pp. 562-566.*
Jon A. Rowley, Gerard Madlambayan, David J. Mooney. Alginate hydrogels as synthetic extracellular matrix materials. Biomaterials 20 (1999) 45-53.*
Tristan Turquois and Hugo Gloria.Determination of the Absolute Molecular Weight Averages and Molecular Weight Distributions of Alginates Used as Ice Cream Stabilizers by Using Multiangle Laser Light Scattering Measurements. J. Agric. Food Chem. 2000, 48, 5455-5458.*
Hirotaka Maruyama, Akio Harada, Tsuyoshi Kurokawa, Hiroyukf Kobayashi, Toshiaki Nonami, Akimasa Nakao, and Hiroshi Takagi. Duration of Liver Ischemia and Hepatic Regeneration after Hepatectomy in Rats. Journal of Surgical Research 58. 290-294 (1995).*
Christian Trautwein, Tim Rakemann, David A. Brenner, Konrad Streetz, Laura Licato, Michael P. Manns, and Gisa Tiegs. Concanavalin A—Induced Liver Cell Damage: Activation of Intracellular Pathways Triggered by Tumor Necrosis Factor in Mice. Gastroenterology 1998;114:1035-1045.*
Anna Gutowska, Byeongmoon Jeong, and Marek Jasionowski. Injectable Gels for Tissue Engineering. The Anatomical Record 263:342-349 (2001).*
Daniel Palmes, Hans-Ullrich Spiegel. Animal models of liver regeneration. Biomaterials 25 (2004) 1601-1611.*
Kaplan Marshall M. and M. Eric Gershwin. Primary Biliary Cirrhosis. N Engl J Med 2005;353:1261-73.*
Gerlach Jorg C, Katrin Zeilinger, and John F Patzer. Bioartificial liver systems: why, what, whither? Regen. Med. (2008) 3(4), 575-595.*
International Preliminary Report on Patentability Dated Jun. 2, 2010 From the International Bureau of WIPO Re. Application No. PCT/IL2008/001552.
International Search Report and the Written Opinion Dated Apr. 23, 2009 From the International Searching Authority Re. Application No. PCT/IL2008/001552.
Cohen et al. "The Pharmacokinetics of, and Humoral Responses to, Antigen Delivered by Microencapsulated Liposomes", Proc. Natl. Acad. Sci. USA, 88: 10440-10444, Dec. 1991.
Earle et al. "Hepatectomy Enables Prolonged Survival in Select Patients With Isolated Noncolorectal Liver Metastasis", Journal of the American College of Surgeons, 203: 436-446, 2006.
Fausto et al. "Liver Regeneration", Hepatology, 43(2/Suppl.1): S45-S53, 2006.
Freeman et al. "The Effect of Sulfation of Alginate Hydrogels on the Specific Binding and Controlled Release of Heparin-Binding Proteins", Biomaterials, 29(22): 3260-3268, 2008.
Geller et al. "Outcome of 1000 Liver Cancer Patients Evaluated at the UPMC Liver Cancer Center", 2005 AHPBA Annual Meeting, Journal of Gastrointestinal Surgery, 10(1): 63-68, 2006.
Khotimchenko et al. "Healing and Preventive Effects of Calcium Alginate on Carbon Terachloride Induced Liver Injury in Rats", Marine Drugs, XP009115181, 2(3): 108-122, 2004. p. 110-111, Experiment 1, p. 111, Table 1, p. 112-114, Experiment 2, p. 114, Table 3.
Kubota et al. "Measurement of Liver Volume and Hepatic Functional Reserve as A Guide to Decision-Making in Resectional Surgery for Hepatic Tumors", Hepatology, 26(5): 1176-1181, 1997.
Landa et al. "Effect of Injectable Alginate Implant on Cardiac Remodeling and Function After Recent and Old Infarcts in Rat", Circulation, 117: 1388-1396, 2008.
Madoff et al. "Portal Vein Embolization in Preparation for Major Hepatic Resection: Evolution of a New Standard of Care", Journal of Vascular and Interventional Radiology, 16(6): 779-790, 2005.
Rowley et al. "Alginate Type and RGD Density Control Myoblast Phenotype", Journal of Biomedical Materials Research, 60(2): 217-223, May 2002.
Sennerby et al. "Acute Tisue Reactions to Potassium Alginate With and Without Colour/Flavour Additives", Biomaterials, 8: 49-52, Jan. 1987.
Shapiro et al. "Novel Alginate Sponges for Cell Culture and Transplantation", Biomaterials, 18(8): 583-590, 1997.
Tsur-Gang et al. "The Effects of Peptide-Based Modification of Alginate on Left Ventricular Remodeling and Function After Myocardial Infarction", Biomaterials, 30(2): 189-195, 2009.
Cohen, S. et al. (1991) "*The Pharmacokinetics Of, And Humoral Responses To, Antigen Delivered by Microencapsulated Liposomes,*" Proc. Natl. Acad. Sci. (USA) 88:10440-10444.
Earle, S.A. et al. (2006) "*Hepatectomy Enables Prolonged Survival in Select Patients with Isolated Noncolorectal Liver Metastasis,*" J. Amer. Coll. Surg. 203(4):436-446.
Fausto, N. et al. (2006) "*Liver Regeneration,*"Hepatology 43(2) Suppl 1:S45-S53.
Freeman, I. et al. (2008) "*The Effect of Sulfation of Alginate Hydrogels on the Specific Binding and Controlled Release of Heparin-Binding Proteins,*" Biomaterials 29(22):3260-3268.
Geller, D.A. et al. (2006) "*Outcome of 1000 Liver Cancer Patients Evaluated at the UPMC Liver Cancer Center,*" J. Gastrointest. Surg. 10(1):63-68.
Khotimchenko,Y.S. et al. (2004)"*Healing and Preventative Effects of Calcium alginate on Carbon Tetrachloride Induced Liver Injury in Rats,*" Marine Drugs MDPI, Basel, CH 2(3):108-122.
Kubota, K. et al. ( ) "*Measurement of Liver Volume and Hepatic Functional Reserve as a Guide to Decision-Making in Resectional Surgery for Hepatic Tumors,*" Hepatology 26(5):1176-1181.
Landa, N. et al. (2008) "*Effect of Injectable Alginate Implant on Cardiac Remodeling and Function After Recent and Old Infarcts in Rat,*" Circulation 117:1388-1396.
Madoff, D.C. et al. (2005) "*Portal Vein Embolization in Preparation for Major Hepatic Resection: Evolution of a New Standard of Care,*" J. Vasc. Interv. Radiol. 16:779-790.
Rowley, J.A. et al. (2002) "*Alginate Type and RGD Density Control Myoblast Phenotype,*" J. Biomed. Mater. Res. 60:217-223.
Sennerby, L. et al. (1987) "*Acute Tissue Reactions to Potassium Alginate With and Without Colour/Flavour Additives,*" Biomaterials 8:49-52.
Shapiro, L. et al. (2002) "*Novel Alginate Sponges for Cell Culture and Transplantation,*" Biomaterials 18(8):583-590.
Tsur-Gang, O. et al. (2009) "*The Effects of Peptide-Based Modification of Alginate on Left Ventricular Remodeling and Function After Myocardial Infarction,*" Biomaterials 30(2):189-195.
International Preliminary Report on Patentability PCT/IL2008/001552 (2010); pp. 1-7.
Office Action Dated Aug. 25, 2011 From the Israel Patent Office Re. Application No. 205935.
Office Action Dated Aug. 7, 2012 From the Israel Patent Office Re. Application No. 205935 and Its Translation Into English.
Communication Pursuant to Article 94(3) EPC Dated Mar. 27, 2013 From the European Patent Office Re. Application No. 08853658.6.
Patent Examination Report Dated May 3, 2013 From the Australian Government, IP Australia Re. Application No. 2008331107.
Office Action Dated Jan. 20, 2014 From the Israel Patent Office Re. Application No. 205935 and Its Translation Into English.
Office Action Dated May 7, 2015 From the Israel Patent Office Re. Application No. 205935 and Its Translation Into English.
Examination Report Dated Mar. 26, 2015 From the Government of India, Patent Office, Intellectual Property Building Re. Application No. 1221/MUMNP/2010.

* cited by examiner

ALGINATE BIOMATERIALS FOR THE TREATMENT OF HEPATIC DISORDERS

FIELD OF THE INVENTION

The invention relates to methods and compositions for promoting in-vivo repair and regeneration of damaged organ tissue, and thus prevention of organ failure, specifically liver failure, based upon the sole either systemic or local application of natural and modified alginate biomaterial in solid or solution forms.

BACKGROUND OF THE INVENTION

All publications mentioned throughout this application are fully incorporated herein by reference, including all references cited therein.

Biomaterials are currently in use or under investigation as implants to facilitate restoration and regeneration of defective or missing tissues in conditions caused by disease, trauma or reconstructive surgical procedures. In particular, injectable biomaterials are ideal for tissue restoration since the flowable material may be delivered via a small incision, allowing minimally invasive access to the tissue space where appropriate. Fluids can interdigitate with the irregular cavity defects (e.g., following surgical procedure) and may, depending on the material used, physically bond to the adjacent tissue. Injectable biomaterials also allow for incorporation and uniform dispersion of cells and/or therapeutic agents, such as growth factors and cytokines that are valuable in enhancing the tissue repair processes.

Additional advantageous features of biomaterials for tissue reconstruction and restoration include their ease of production and handling compared to the processes involving cells and their being off-the-shelf products. Biomaterials, especially those derived from plant/algae, such as the alginate polysaccharides, are non immunogenic, biocompatible, biodegradable and not affected by age or disease. They are relatively low cost as compared to existing cell therapy approaches.

The primary considerations for injectable scaffolds for utilities such as bulking, filling voids and tissue reconstruction include mechanical strength and durability, promotion of tissue formation, biodegradability, biocompatibility, sterilizability, minimal setting time and temperature change, low viscosity for easy injection, as well as ease in accessing the defect. The scaffold must exhibit the necessary mechanical properties as well as provide physical support. Preferably, the scaffold would promote matrix formation while degrading over time. The biocompatibility of the material is also of great importance. Neither the initial material nor its degradation products should elicit an unresolved immune response, promote immunotoxicity, or express cytotoxicity. To minimize infections and related immune responses, the implanted material must be easily sterilized while retaining the original bioactivity and chemical composition.

The candidate biomaterials can be injected as viscous fluids and then cured by methods such as thermosensitive or pH-sensitive crosslinking, photopolymerization, or addition of a solidifying agent to form a gel-like substance. The biomaterials can be also implanted as pre-formed solid matrix, as hydrogel or macroporous scaffold.

The present invention describes a method for replacing or supplementing lost organ function using therapeutical biomaterials. Such method is advantageous over pharmacological manipulation or transplantation of whole organ or parts of organ, as the later do not cure a disease but rather modify its outcome, or trade the original disease for the complications of non-specific immunosuppression.

Every structure in living organisms is in a dynamic state of equilibrium, undergoing constant renewal, remodeling and replacement of functional tissue which vary from organ to organ and structure to structure. Following extensive damage, these abilities of remodeling and replacement are greatly impaired. Biomaterials provide temporary scaffoldings for remaining organ tissue cells, and thereby allow the cells to secrete extracellular matrix and to enable, in the long term, a complete and natural tissue replacement. The macromolecular structure of these biomaterials is selected so that they are completely degradable and are eliminated, once they have achieved their function of providing the initial artificial support for the remaining organ tissue cells. For these biomaterials to be useful in cell transplantations, they must be highly porous with large surface/volume ratios to accommodate a large number of cells, they must be biocompatible, i.e., non-toxic to the host tissue into which they are transplanted, they must be capable of promoting cell adhesion and allowing the retention of the differentiated function of attached cells.

Alginate is an anionic polysaccharide derived from brown algae. It is a block co-polymer of mannuronic acid (M) and guluronic acid (G). The polymer is widely used in the pharmaceutical, food and medical industries. The sodium salt of alginate is soluble in water and in the presence of divalent cations, such as calcium ions, it forms hydrogel at room temperature.

More specifically, alginates have been used previously for the purpose of cell transplantation. Alginates are natural polysaccharide polymers, the word "alginate" actually referring to a family of polyanionic polysaccharide copolymers derived from brown sea algae and comprising 1,4-linked β-D-mannuronic (M) and α-L-guluronic acid (G) residues in varying proportions. Alginates are soluble in aqueous solutions, at room temperature, and are capable of forming stable gels, particularly in the presence of certain divalent cations such as calcium, barium, and strontium. The unique properties of alginates, together with their biocompatibility [see Sennerby, L. et al. Biomaterials 8:49-52 (1987) and Cohen, S. et al. Proc. Natl. Acad. Sci. USA (In Press) 88 (23):10440-10444 (1991)], relatively low cost and wide availability have made them important polymers in medicinal and pharmaceutical applications.

WO97/44070 by some of the present inventors, describes implantable polysaccharide, e.g. alginate sponges for use as a matrix, substrate or scaffold for the cultivation of mammalian cells in vitro prior to their implantation to replace damaged or removed tissue. WO2004/098669 also by part of the present inventors describes injectable cross-linked alginate, which forms a hydrogel in vivo. This cross-linked alginate solution was shown as effective in repair of cardiac tissue damage and ablation of cardiac arrhythmias, when locally applied onto the cardiac tissue.

Surprisingly, and in contrast, the present invention now shows that the alginate biomaterial as a solid, hydrogel, liquid (cross-linked as well as non-cross-linked) is by itself sufficient for the in vivo promotion of repair and regeneration of damaged tissue, decreasing the cellular damage and restoring organ synthetic functions to near-normal levels. Moreover, using non-cross-linked alginate solution, the invention demonstrates for the first time that systemic application, by an i.p. injection, leads to recovery of liver functions, and therefore is feasible for treating liver associated disorders.

The ability of the liver to regenerate itself enables it to overcome various forms of injuries [see Fausto, N. et al. Hepatology 43 (2Suppl 1):S45-53 (2006)]. Partial hepatectomy in humans is often needed and well tolerated in the setting of primary of secondary liver tumors [see Geller, D. A. et al. J. Gastrointest Surg. 10 (1):63-8 (2006)]. Nevertheless, there are cases in which extended partial hepatectomy is warranted due to large hepatic mass and pose a high risk for fulminant hepatic failure [see Kubota, K. et al. Hepatology 26 (5):1176-81 (1997)]. In these cases liver transplantation is the only option for treatment. To avoid this risk, innovative therapies such as portal vein embolization and staged liver resections have been both used, and were shown to be associated with considerable morbidity and mortality [see Madoff, D. C. et al. J. Vasc. Interv. Radiol. 16 (6): 779-90 (2005); and Earle, S. A. et al. J. Am. Coll. Surg. 203 (4):436-46 (2006)].

The alginate biomaterial solutions are ideal candidates for use as implants to facilitate restoration and regeneration of defective or missing tissues since they can be injected as low viscosity solution and can solidify on site [Landa, N. et al., Circulation 117:1388-1396 (2008)]. There is no need for additional curing methods, such as thermo-sensitive cross-linking or pH-sensitive cross-linking, photopolymerization, or addition of solidifying agents. It should be appreciated that most of these curing methods have drawbacks, for example, polymers that cure through a photopolymerization could pose a problem due to a limited ability to access the small cavities with light needed to initiate cross-linking.

Alginate biomaterials can further be manipulated by modification with adhesion peptides, such as RGD, to make them more adhesive, thus enhancing their interactions and integration with the host. For example, alginate modification with RGD reversed this polysaccharide from being cell-inert to a polysaccharide having cell adhesion promoting properties. Such modifications may be better interdigitate with the host [Tsur-Gang, O. et al., Biomaterials 30 (2):189-195 (2009)]. In addition, biomaterials can be designed to enable the controlled delivery of therapeutic agents, such as growth factors and cytokines.

In search for efficient agents for in vivo, physical and functional repair of the damaged tissue, preferably an agent used systemically, the present inventors unexpectedly found that aqueous solutions of uncross-linked or calcium cross-linked alginate as well as solid forms of calcium-alginate hydrogels or sponges are able to facilitate functional restoration and regeneration of damaged liver following an extensive (90%) partial hepatectomy (PH) or following an immune mediated hepatitis.

It is thus an object of the present invention to provide a method for the treatment of liver damage and failure following extensive injury that employs a systemically injectable or in situ locally implantable biocompatible alginate biomaterial to support and regenerate the failing liver.

Another object of the invention to provide methods using alginate biomaterial in the treatment of subjects suffering from severe impairment of hepatic functions due to compulsory extensive partial hepatectomy or other acute or chronic liver disease.

These and other objects of the invention will become apparent as the description proceeds

SUMMARY OF THE INVENTION

In a first aspect, the present invention relates to a method for the treatment of hepatic disorders in a subject in need thereof. The method of the invention comprises the step of administering to said subject, preferably, by a systemic administration, a therapeutically effective amount of at least one biocompatible alginate biomaterial, any modification thereof and any combination thereof.

In one specific embodiment, the method of the invention is applicable to a subject suffering from impaired liver function resulting from fulminant hepatic failure, liver disease and/or hepatectomy.

In another aspect, the invention provides a method for sustaining serum albumin levels and/or lowering the levels of any one of serum ALT and AST levels in a subject suffering of hepatic disorder. The method of the invention comprises the step of administering, preferably in a systemic manner, to said subject, a therapeutically effective amount of at least one biocompatible alginate biomaterial, any modification thereof and any combination thereof.

In yet another aspect, the invention relates to a method for reducing the level of apoptosis, in a damaged liver tissue of a subject suffering of hepatic disorder. The invention further provides a method for increasing cell proliferation in a damaged liver tissue of a subject suffering of hepatic disorder. The method of the invention comprises the step of administering, preferably by a systemic manner, to the treated subject, a therapeutically effective amount of at least one biocompatible alginate biomaterial, any modification thereof and any combination thereof.

In yet another aspect, the invention relates to at least one biocompatible alginate biomaterial, any modification thereof and any combination thereof for use in the treatment of hepatic disorders.

A further aspect of the invention relates to the use of a therapeutically effective amount of at least one biocompatible alginate biomaterial, any modification thereof and any combination thereof for the preparation of a pharmaceutical composition for the treatment of hepatic disorders in a subject in need thereof.

These and other aspects of the invention will become apparent by the hand of the following examples.

Figure shows scanning electron microscope (SEM) micrographs of alginate (FIG. 1A) and collagen (FIG. 1B) macroporous scaffolds.

Figure 2A:
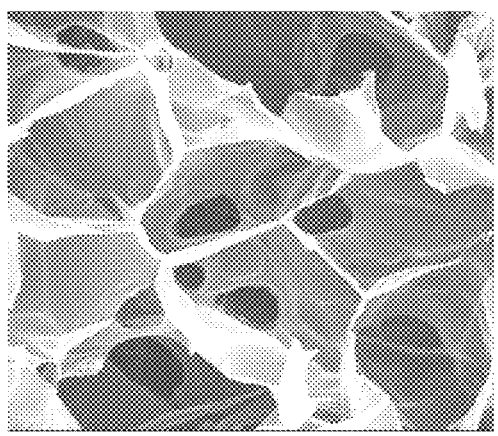
Figure 2B:
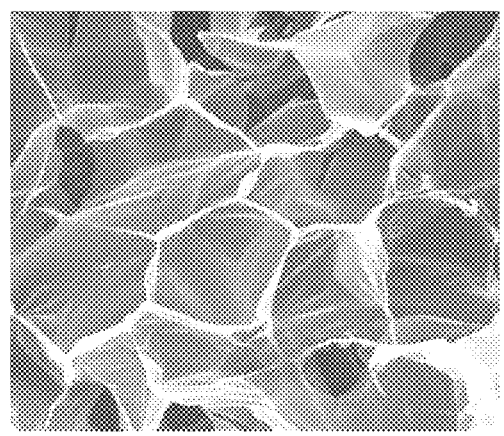

FIG. 2A-2B: Modified Alginate structure

SEM micrographs of cross-sections in macroporous scaffolds prepared from unmodified (FIG. 2A) and RGD-decorated (FIG. 2B) alginate Bar=50 μm.

Figure 3:
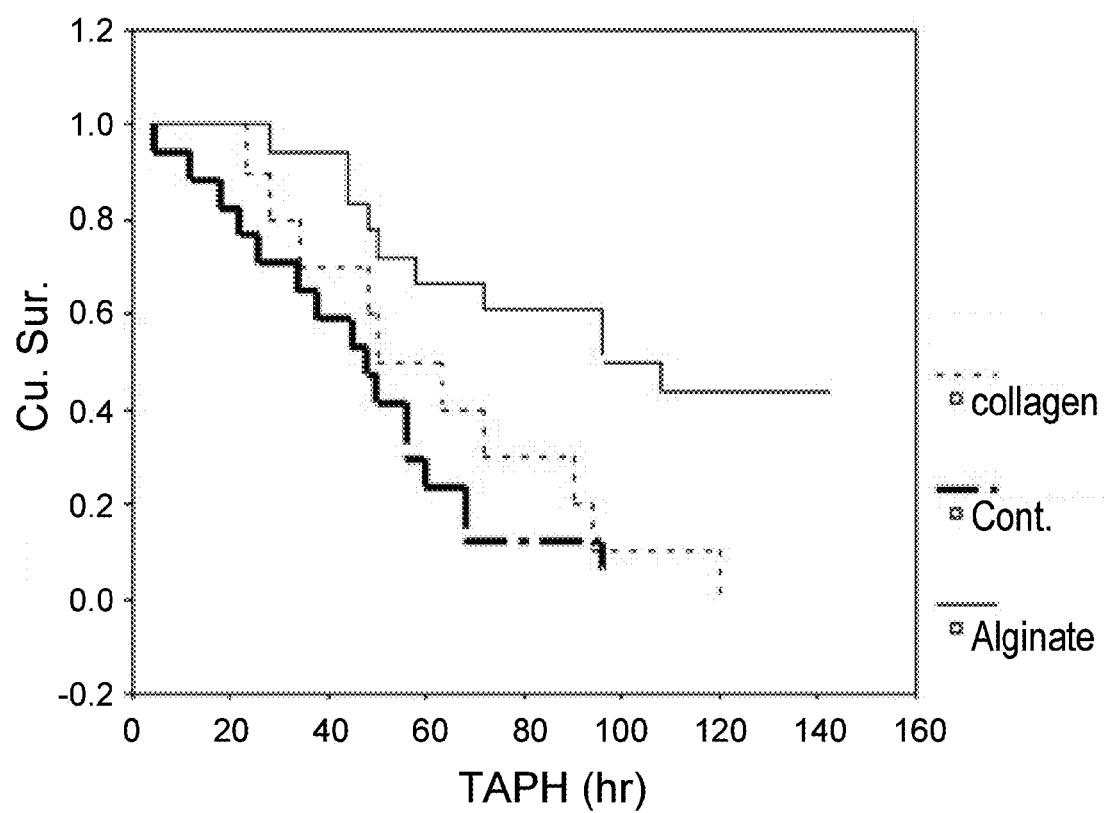

FIG. 3: Kaplan-Meir survival curve

Kaplan-Meir survival curve comparing mice treated with alginate scaffold, collagen scaffold and no scaffold. Survival significantly decreased when collagen or no scaffold were used (log rank=0.001). There was no significant difference in survival between mice with collagen scaffold and no scaffold. Abbreviations: Cu. Sur. (Cumulative Survival); TAPH (time after partial hepatectomy), Cont. (control with no scaffold).

Figure 4:
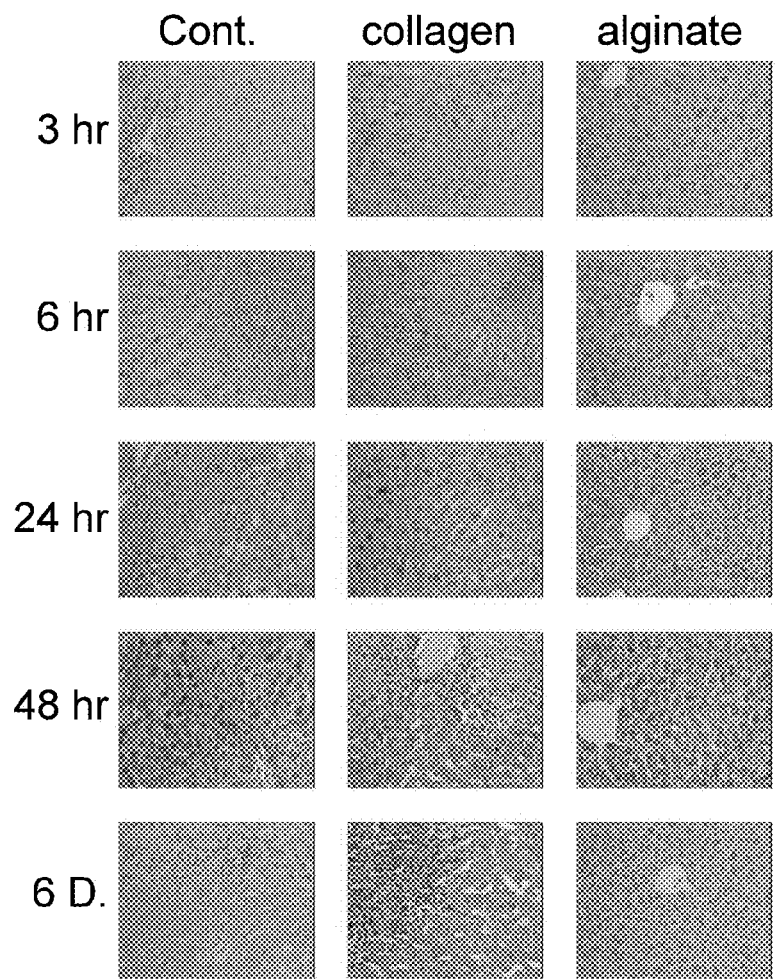

FIG. 4: tissue: Alginate scaffold improves damaged tissue structure

Figure shows a representative H&E staining of liver in various time points after 87% partial hepatectomy obtained from mice treated with collagen (n=4), alginate (n=4) and control mice with no scaffold (n=4). Abbreviations: cont. (control, no scaffold), hr (hours), D (days).

Figure 5A:
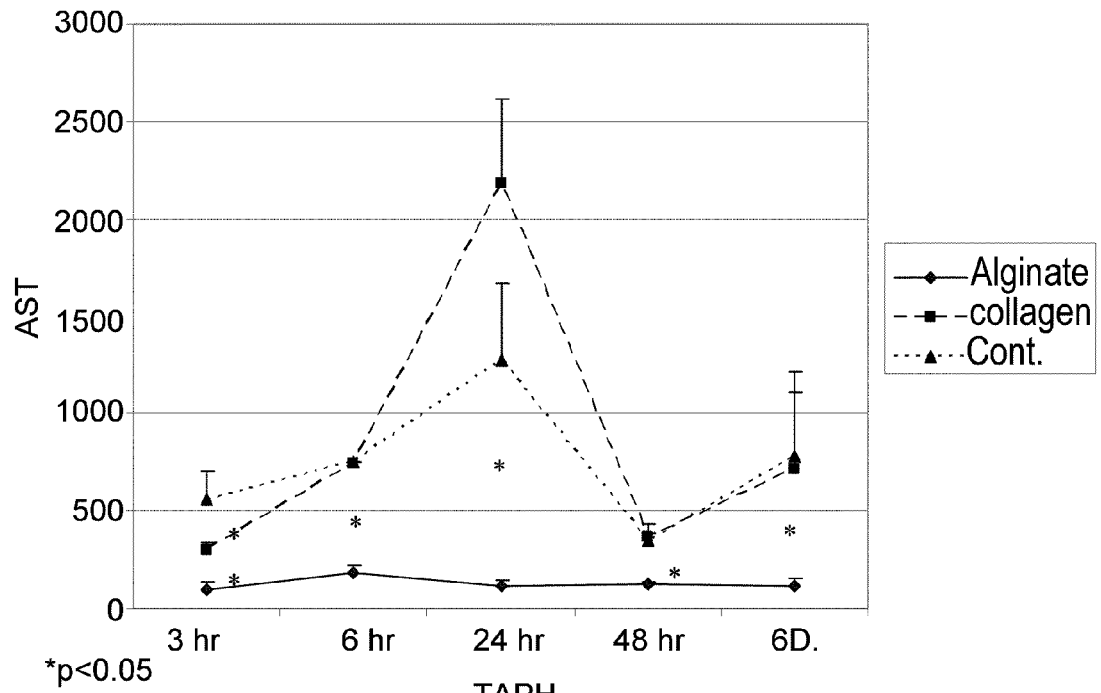
Figure 5B:
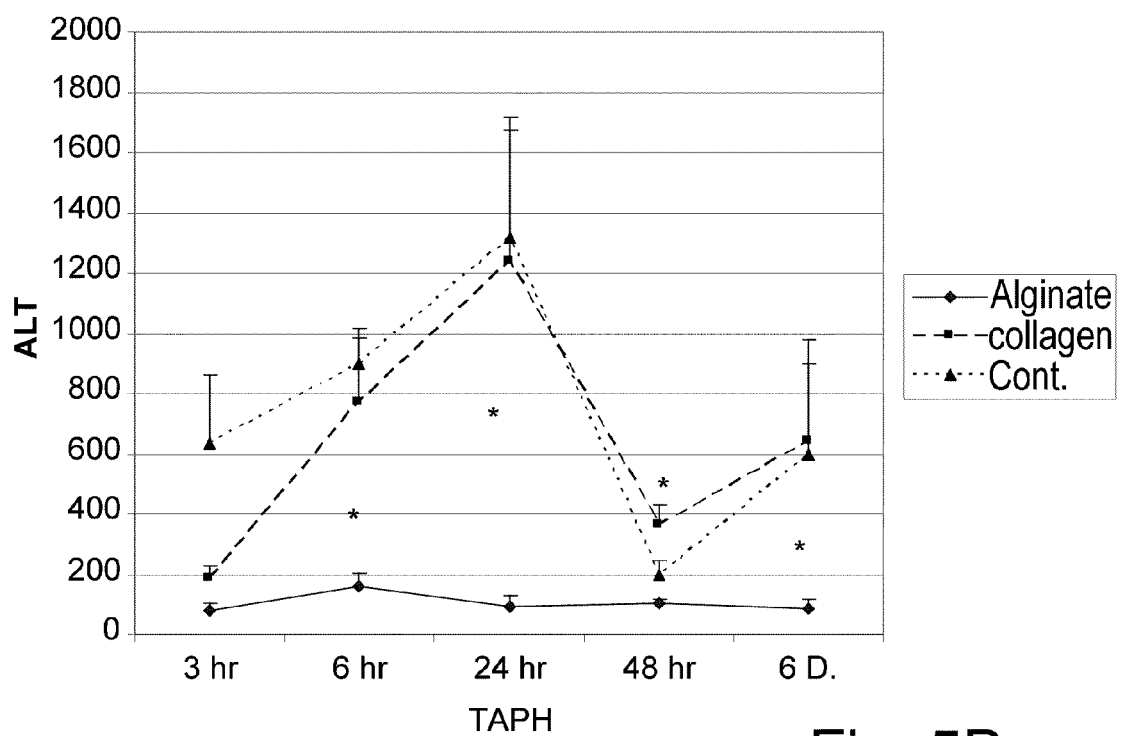

FIG. 5A-5B: Changes in ALT and AST levels in response to alginate scaffold treatment Graphs depicting changes in AST (FIG. 5A) and ALT (FIG. 5B) levels in mice with no scaffold (control), alginate scaffold and collagen scaffold at 3, 6, 24, 48 hours and 6 days after hepatectomy of 87% of the liver. Abbreviations: AST (serum AST levels), ALT (serum ALT levels), cont. (control, no scaffold), hr (hours), D (days), TAPH (time after partial hepatectomy).

Figure 6:
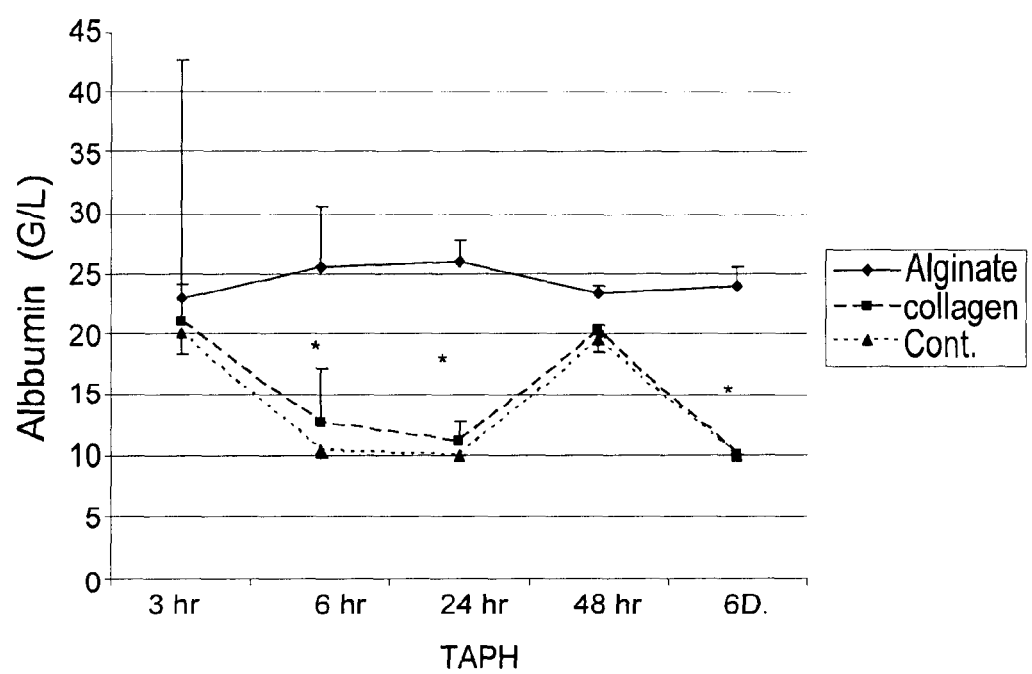

FIG. 6: changes in serum albumin levels in response to alginate scaffold treatment Graph depicting changes in serum albumin levels in mice with no scaffold (control), alginate scaffold and collagen scaffold at 3, 6, 24, 48 hours and 6 days after hepatectomy of 87% of the liver. Abbreviations: cont. (control, no scaffold), hr (hours), D (days), TAPH (time after partial hepatectomy).

Figure 7A:
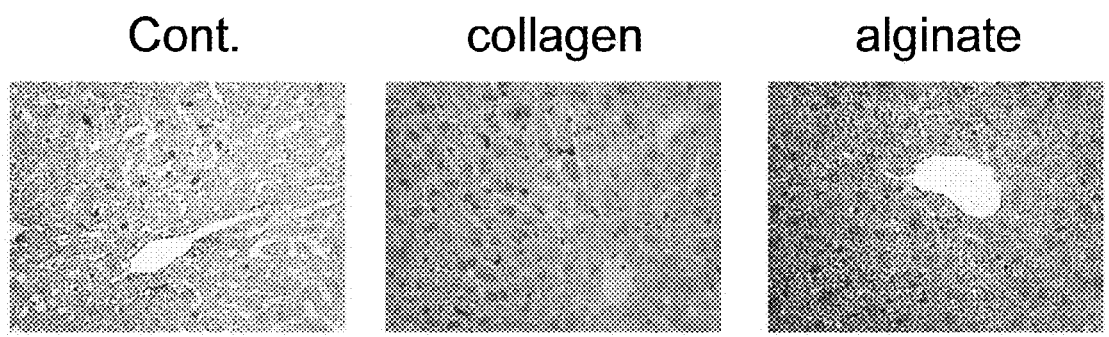
Figure 7B:
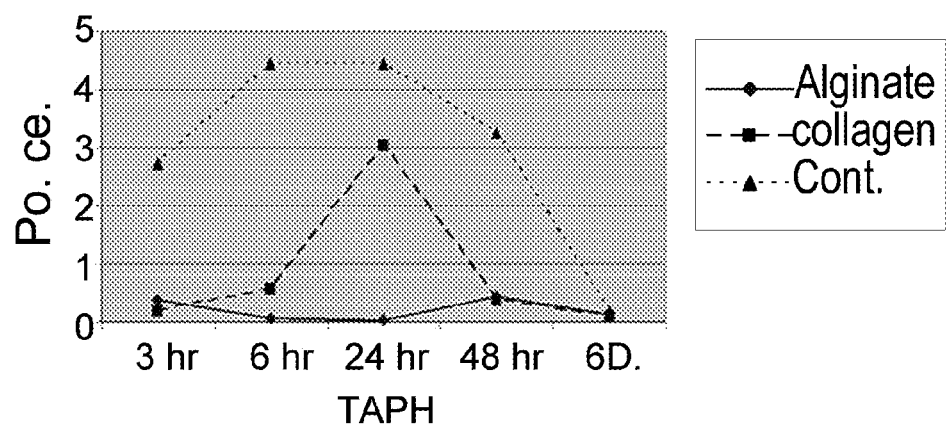

FIG. 7A-7B: Alginate scaffolds lead to reduced apoptosis

FIG. 7A shows immunohistochemical staining for caspase-3 of liver tissue samples obtained 24 hours after 87% partial hepatectomy from mice treated with collagen, alginate scaffold and with no scaffold (control).

FIG. 7B shows a graph quantitating the amount of Caspase-3 positive apoptotic cells in samples of the three experimental groups obtained 3, 6, 24, 48 hours and 6 days after extensive hepatectomy. Abbreviations: cont. (control, no scaffold), hr (hours), D (days), TAPH (time after partial hepatectomy), po. (positive), ce. (cells).

Figure 8:
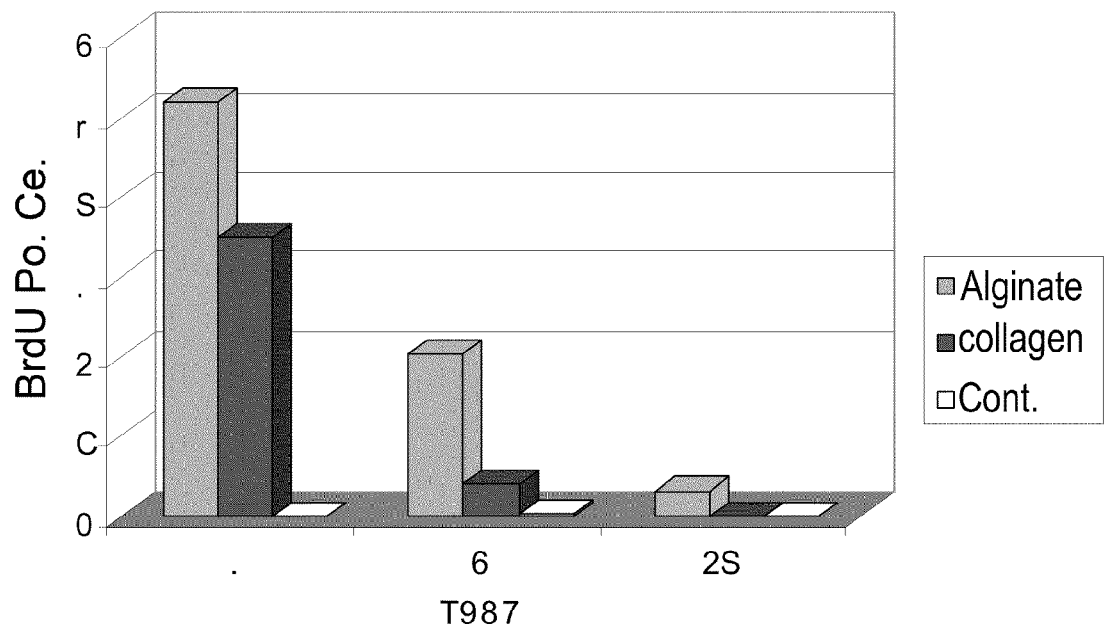

FIG. 8: Alginate scaffold increases cell proliferation

Histogram demonstrates quantification of BrdU positive cells in samples obtained 3, 6 and 24 hours after 87% partial hepatectomy from mice treated with collagen, alginate scaffold and with no scaffold (control). Abbreviations: cont. (control, no scaffold), TAPH (time after partial hepatectomy), po. (positive), ce. (cells).

Figure 9:
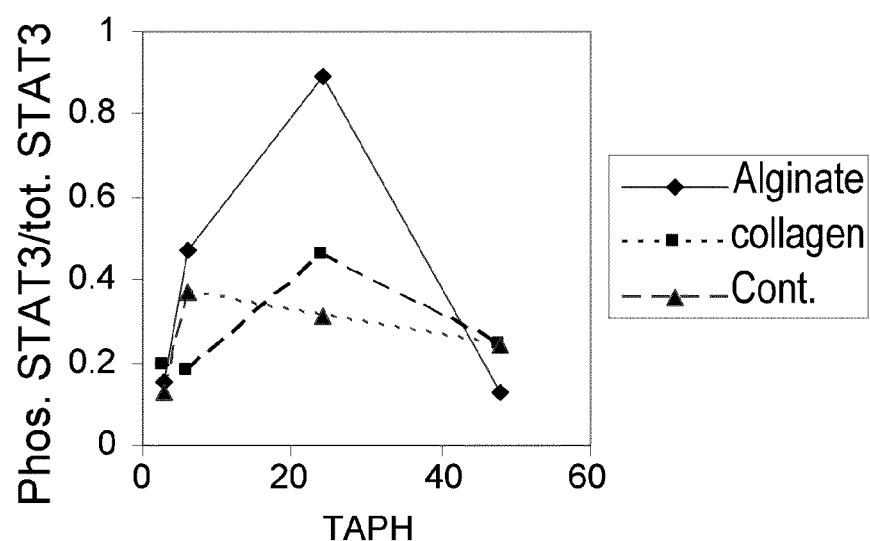

FIG. 9: Alginate scaffold increases activation of STAT3

Graph shows histogram presenting the phosphorylated STAT 3/total STAT3 ratio as obtained by densitometry of immuno-blot incubated with anti-phosphorylated STAT3 and anti STAT3 antibodies. Abbreviations: cont. (control, no scaffold), TAPH (time after partial hepatectomy), phos. (phosphorylated), tot. (total).

Figure 10:
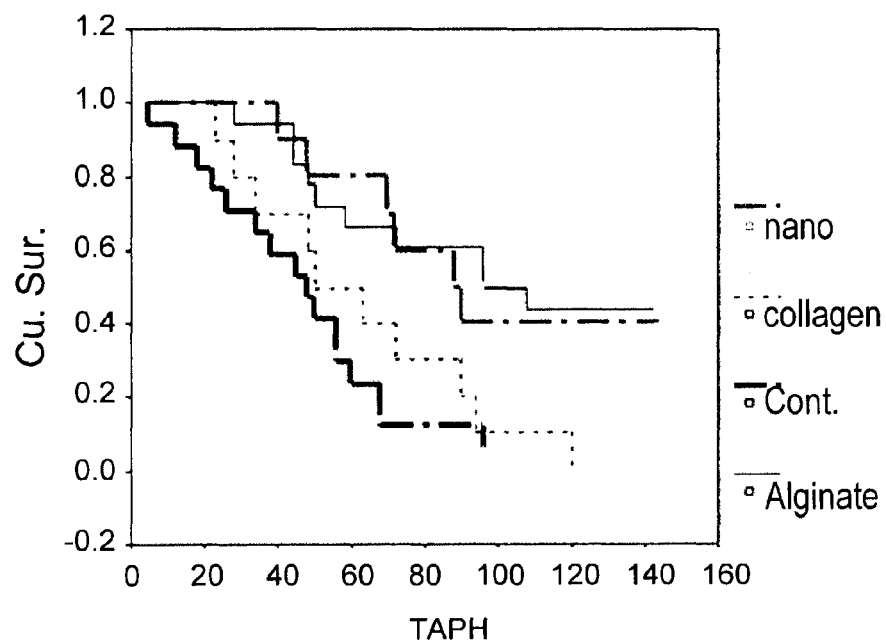

FIG. 10: Nano-pores and macro-pores alginate scaffolds increase mice survival

Kaplan-Meir survival curve comparing survival in different time points (hours) after hepatectomy of mice treated with alginate scaffold (macro-pores), nano-pores alginate scaffold, collagen scaffold or no scaffold control. Abbreviations: Cu. Sur. (Cumulative Survival), TAPH (time after partial hepatectomy), cont. (control), nano (nano-alginate scaffold), alginate (macro-alginate scaffold).

Figure 11:
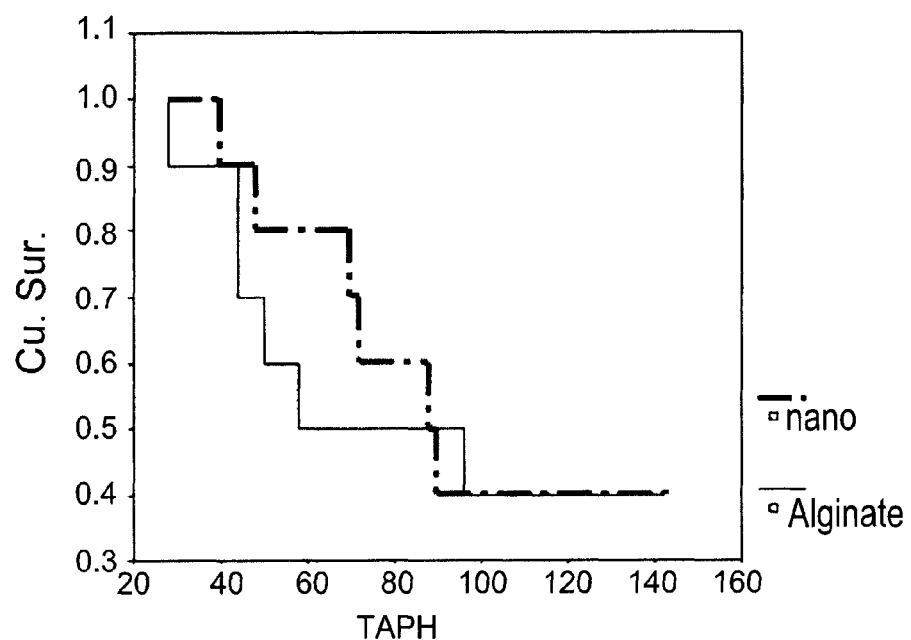

FIG. 11: Nano-pores and macro-pores alginate scaffolds increase mice survival

Kaplan Meir Survival curve comparing nano-pores alginate scaffold to macro-pores alginate scaffolds, showing no difference in survival between the two groups (log-rank=0.8). Abbreviations: Cu. Sur. (Cumulative Survival), TAPH (time after partial hepatectomy), nano (nano-alginate scaffold), alginate (macro-alginate scaffold).

Figure 12A:
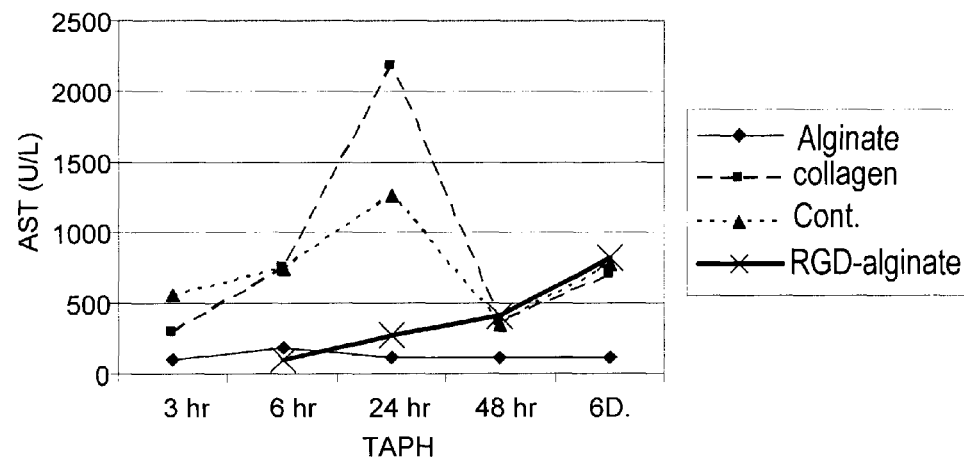
Figure 12B:
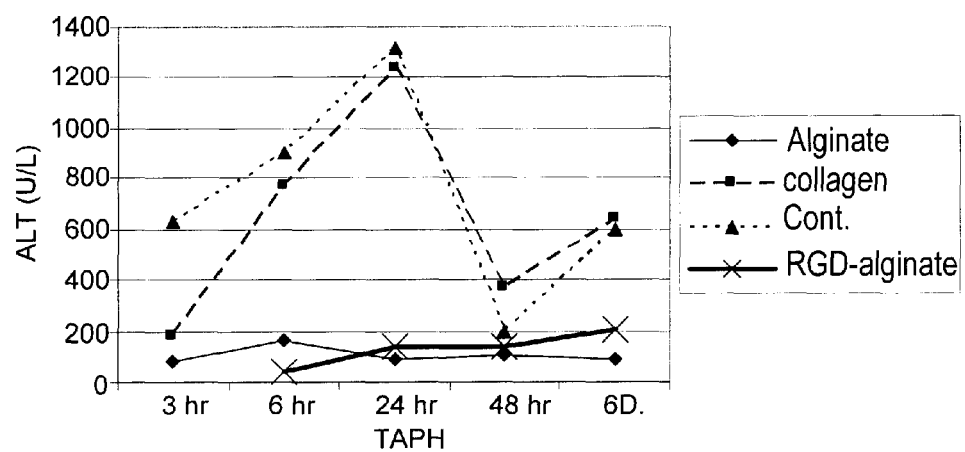

FIG. 12A-12B: Changes in ALT and AST levels in response to RGD decorated alginate scaffold treatment Graphs depicting changes in AST (FIG. 12A) and ALT (FIG. 5B) levels in mice with no scaffold, alginate scaffold, RGD-decorated alginate scaffold and collagen scaffold at 3, 6, 24, 48 hours and 6 days after hepatectomy of 87% of the liver. Abbreviations: AST (serum AST levels), ALT (serum ALT levels), cont. (control, no scaffold), hr (hours), D (days), TAPH (time after partial hepatectomy).

Figure 13:
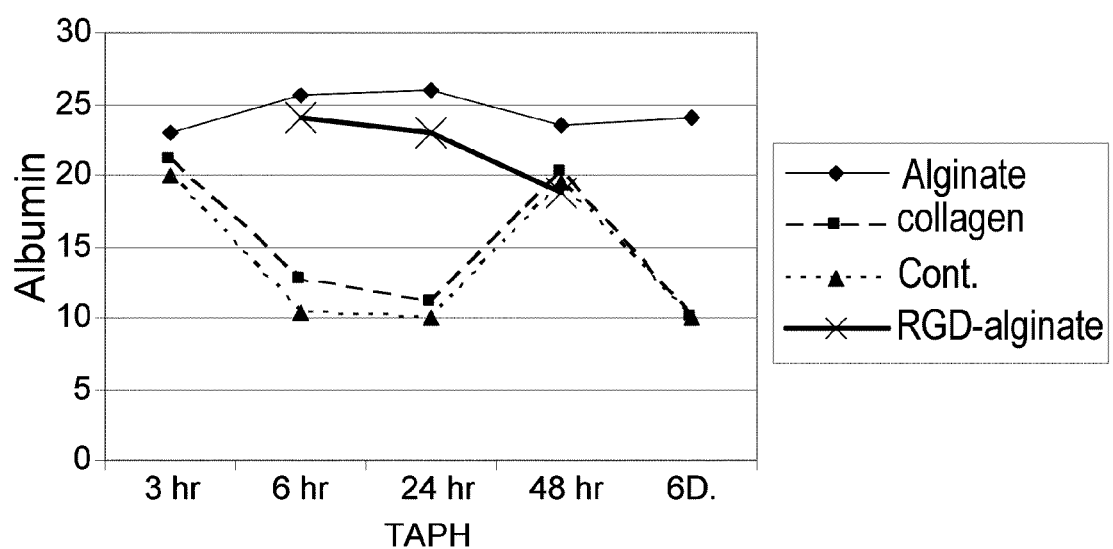

FIG. 13: Changes in serum albumin levels in response to RGD-Alginate scaffold treatment Graph depicting changes in serum albumin levels in mice with no scaffold (control), alginate scaffold, RGD-decorated scaffold and collagen scaffold at 3, 6, 24, 48 hours and 6 days after hepatectomy of 87% of the liver. Abbreviations: cont. (control, no scaffold), hr (hours), D (days), TAPH (time after partial hepatectomy).

Figure 14A:
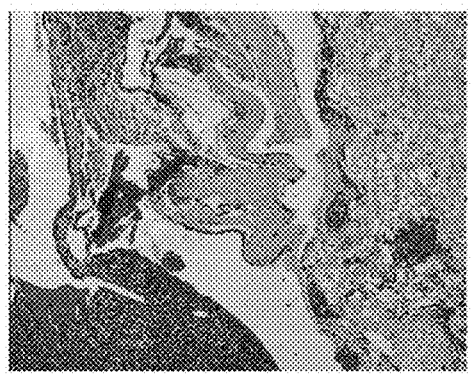
Figure 14B:
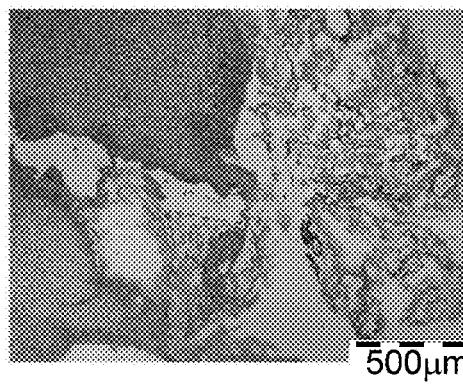
Figure 14C:
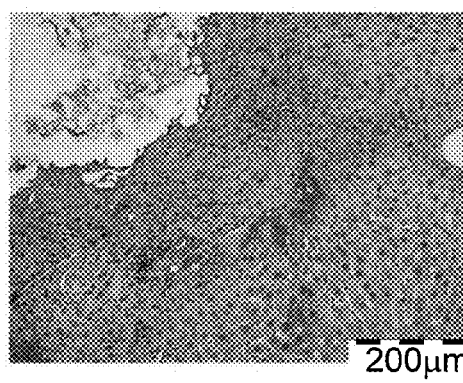

FIG. 14A-14C: Localization of the alginate scaffold in the damaged liver tissue

H&E staining of representative liver section from a mouse 24 hours after 87% PH with alginate scaffold (FIG. 14A) and immuno-histochemistry for biotin of liver from mouse with biotin labeled alginate scaffold 3 hours (FIG. 14B) and 6 hours (FIG. 14C) after PH.

Figure 15:
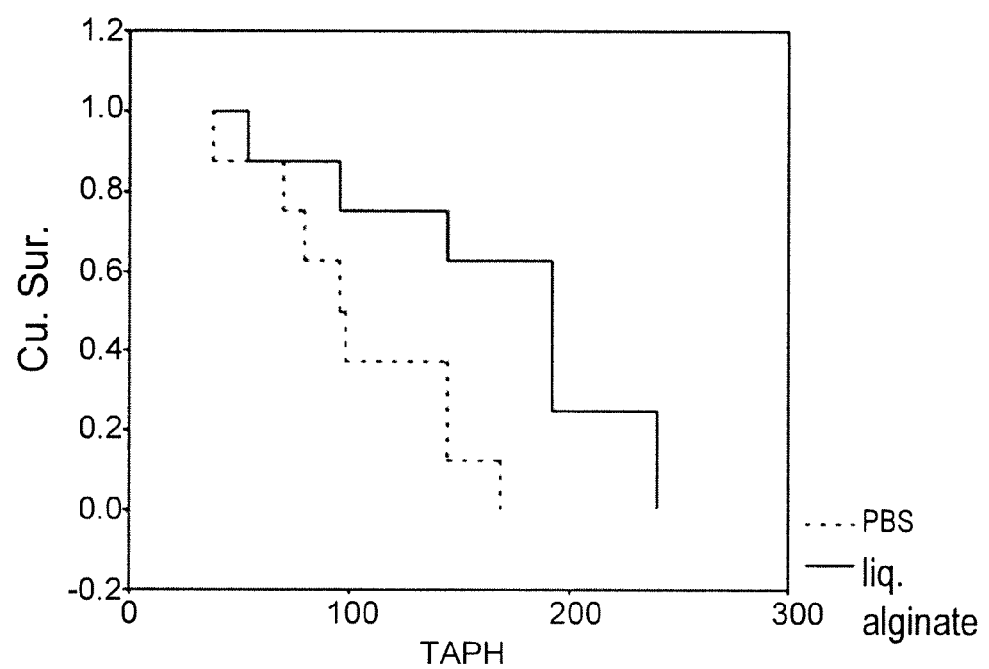

FIG. 15: Liquid non-cross-linked alginate increases mice survival

Kaplan Meir survival curve comparing survival of mice (n=10) treated with liquid alginate vs. PBS control after 87% partial hepatectomy showing significant improvement of survival in the alginate treated group (log rank=0.001). Abbreviations: Cu. Sur. (Cumulative Survival), TAPH (time after partial hepatectomy), liq. (liquid).

Figure 16A:
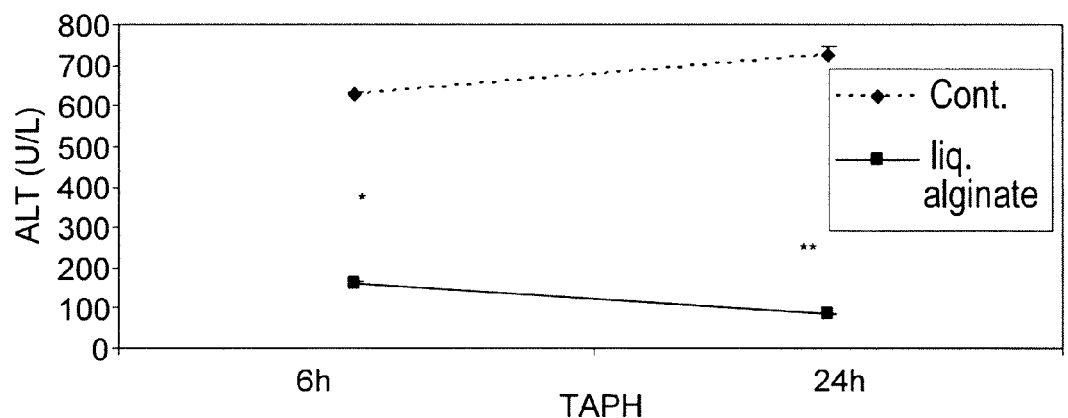
Figure 16B:
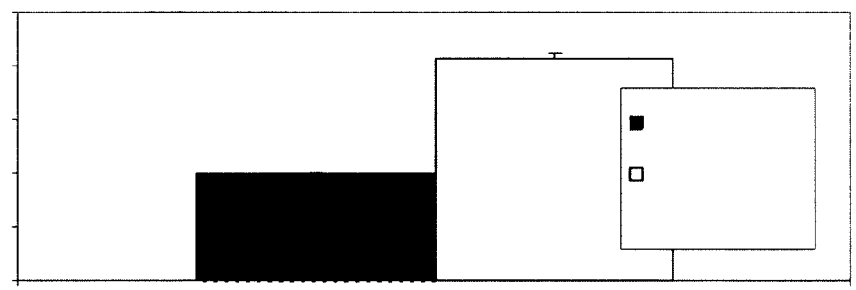

FIG. 16A-16B: Changes in ALT and serum albumin levels in response to liquid-alginate treatment FIG. 16A shows serum ALT levels of samples obtained from mice treated with liquid non-cross-linked alginate vs. PBS control after 87% partial hepatectomy. FIG. 16B shows serum albumin levels of both experimental groups. $*p=0.000001$; $p=0.000001$; $*p=0.01$. PHx=partial hepatectomy. Abbreviations: cont. (control), liq. (liquid), TAPH (time after partial hepatectomy), h (hours).

Figure 17A:
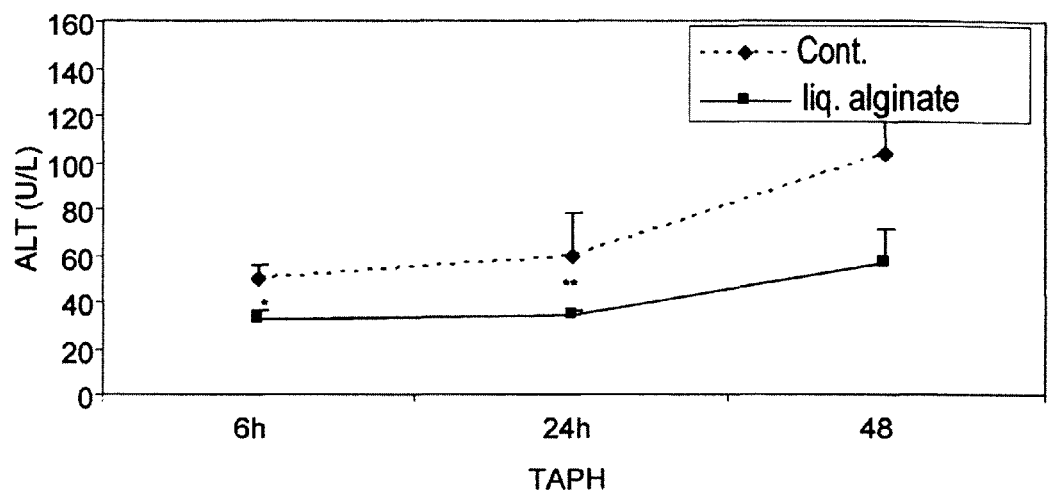
Figure 17B:
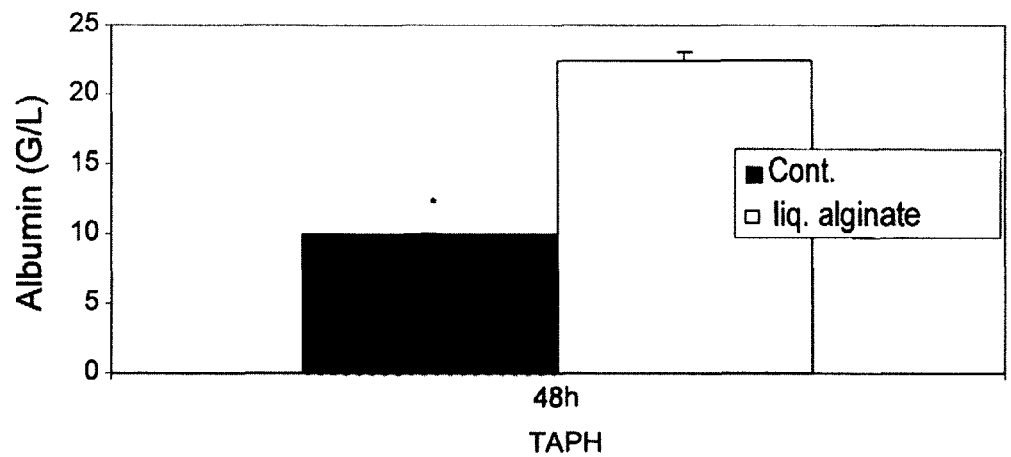

FIG. 17A-17B: Changes in ALT and serum albumin levels in ConA hepatitis treated with liquid-alginate The effect of liquid alginate on the induction of immune mediated hepatitis by ConA is assessed by serum ALT levels 6, 24 and 48 hours after conA administration (FIG. 17A), and serum albumin 48 hours after conA (FIG. 17B). Liquid alginate was injected intraperitoneal (i.p.) two hours prior to ConA administration. $*p=0.004$; $**p=0.04$.

Abbreviations: cont. (control), liq. (liquid), TAPH (time after partial hepatectomy).

DETAILED DESCRIPTION OF THE INVENTION

The present invention firstly demonstrates that alginate biomaterials have significant effect on survival after acute liver failure due to extended 87% hepatectomy. As shown by the following examples, mice treated with alginate biomaterials were protected from hepatocellular injury, hepatic necrosis and apoptosis, and moreover, exhibited improved hepatic synthetic function. BrdU staining suggests that alginate biomaterial improves regeneration early after hepatectomy and biotin-labeled alginate scaffold shows that alginate biomaterial invades the hepatic parenchyma. The use of nanopores alginate hydrogel and macroporous scaffolds made from unmodified alginate and RDG-alginate showed comparable therapeutic results, suggesting that the alginate biomaterial itself rather than the matrix pore size or physical state (solution or solid) plays a role in its therapeutic effect. Phospho-STAT levels indicate that these effects may be mediated by the IL6-TNFα-STAT3 cascade. Moreover, the present invention further shows for the first time that alginate may be further applicable in immune-related damage of hepatic tissue for example, when the ConA induced hepatitis model was used.

It should be further noted that the implantation or injection, preferably a systemic application, of an acellular alginate scaffold or solution by itself into animals suffering of severely impaired organ functions, specifically, liver, as a result of tissue damage, removal or dysfunction, significantly elevated their survival, decreased the degree of cellular damage and improved synthetic functions to near-normal levels.

Partial resection of damaged organ tissue is often warranted and well tolerated in the setting of primary and secondary tumors, severely impaired functioning or various diseases. However, cases in which extended resection is necessary pose a risk of fulminant organ failure which may be treated only by organ transplant. Donor scarcity limit the number of patients who may benefit from such procedures and the considerable morbidity and mortality associated with the latest innovative therapies, require the finding of an alternative method of treatment.

Thus, according to a first aspect, the present invention relates to a method for the treatment of hepatic disorders in a subject in need thereof. More specifically, the method of the invention comprises the step of administering to said subject a therapeutically effective amount of at least one biocompatible alginate biomaterial, any modification thereof and any combination thereof. The effective amount of the alginate sponge, hydrogel or solution should be sufficient for promoting repair and regeneration of the damaged organ tissue.

It should be noted that the administration or application step may be performed either locally or systemically. The term "administration" includes applying to, implanting, spraying, bandaging, injecting or introducing to said subject, or if locally applied to a liver tissue of the treated subject. According to one embodiment, the method of the invention may be specifically effective in repairing and/or regenerating damaged organ, specifically, liver tissue in a subject in need thereof.

The invention relates to the use of bioresorbable biocompatible alginate in the form of sponges, hydrogels or liquid solutions, whose macro-molecular or nano-molecular structure is such that they are completely degraded and eliminated, and is non-toxic to the host organ tissue into which they are implanted, administered, sprayed, injected or introduced.

It should be further appreciated that the terms "sponge" and "scaffold" are used herein interchangeably. It should be further noted that these terms also encompass the alginate hydrogel and alginate solutions after their deposition in the target tissue. As demonstrated by the biotin-labeled alginate scaffold derivative presented by FIG. 14, in a preferred embodiment, the biodegradable alginate sponges degrade slowly in vivo to provide an artificial support which is stable for sufficient time to allow invasion and proliferation by surrounding tissue cells and blood vessels.

It should be appreciated that the biocompatible alginate biomaterials of the invention may be preferably used alone as an implant or alternatively, as a first stage of an implant which is stable for sufficient time to allow for vascularization by surrounding-tissue-blood-vessels. Once vascularized, the implant becomes accessible to the second stage of injection there into of a sufficient amount of cells of choice (e.g. hepatocytes) either grown in vitro or obtained from the host, or a suitable donor, said cells being capable of rapid acclimization and proliferation on the vascularized sponge to rapidly replace the damaged tissue.

As used herein the term "implantation", refers to the insertion of an alginate sponge, scaffold or any modification thereof, into a patient in need thereof as a result of tissue damage, removal or dysfunction. As shown by Example 5, where the liquid alginate solution is used, the administration of the alginate may be by applying, specifically, spraying the liquid alginate onto the damaged tissue. Alternatively, as shown by Example 6, the liquid alginate may be administered by injection, more specifically, i.p. injection to the treated subject. It should be appreciated that this example demonstrates the feasibility of systemic application of the alginate biomaterial for treating hepatic disorders.

Although i.p. (intraperitoneal) injection is preferred, it should be noted that the administration step may include intraperitoneal, parenteral, intravenous, intramuscular, subcutaneous, transdermal, intranasal, mucosal, topical or subcutaneous administration, or any combination thereof. It should be further noted that the liquid alginate solution can be administered by injection (with a syringe and a needle), catheterization (through catheters or shunts), or any suitable percutaneous hepatic delivery system which includes hepatic delivery device with a guidewire, including electromechanical mapping or MRI guided catheters, and any further suitable method and means for administration of a fluid into any part of the body of a subject in need, particularly non-surgical methods. Thus, the alginate solution of the invention may be administered to a subject in need by any one of the means detailed herein above.

Such insertion or application requires that the biocompatible alginate biomaterial be contacted by surrounding tissue cells and blood vessels by placing a sufficient amount of alginate sponges, hydrogels or solutions (un crosslinked or crosslinked) either systemically or locally, onto organ-tissue favorable beds for engraftment either by gluing or suturing using non-toxic, hypoallergenic natural or synthetic adhesives, bioresorbable sutures, spraying a liquid composition or injecting of injectable compositions of polymeric solutions capable of self assembly into the alginate scaffold or hydrogel in vivo.

According to one embodiment, the alginate biomaterial used by the method of the invention may be in the form of any one of alginate solution, alginate hydrogel, solid alginate sponge or any combinations thereof.

According to one embodiment, the alginate biomaterial used by the invention may be an alginate polysaccharide characterized by having at least one of: (a) a mannuronic acid (M) residue content in the range of between about 0% and about 100% of total residues, between about 0, 5, 10, 15, 20, 25, 30, 35, 40, 45, 50, 55, 60, 65, 70, 75, 80, 85, 90, 95, 100, preferably between about 25% to 65%; (b) a guluronic acid (G) residue content in the range of between about 0% and about 100% of total residues, between about 0, 5, 10, 15, 20, 25, 30, 35, 40, 45, 50, 55, 60, 65, 70, 75, 80, 85, 90, 95, 100, preferably between about 35% to 75%; and (c) a molecular weight between about 1000 to 300,000 Dalton, preferably, between about 1000, 10,000, 15,000, 20,000, 25,000, 30,000, 35,000, 40,000, 45,000, 50,000, 60,000, 70,000, 80,000, 90,000, 100,000, 150,000, 200,000, 250,000, 300,000 Dalton. According to one particular embodiment, injectable liquid alginate solution may be characterized by having a molecular weight of between about 1000 to about 50,000 Dalton. In another embodiment, for hydrogel or sponges, preferred molecular weight range is 5000 to 100,000 Dalton.

In a preferred embodiment, the alginate used by the method of the invention may be derived from brown sea algae selected from the group consisting of alginate MVG™ (MVG) derived from *Laminaria hyperborea*, alginate LVG™ derived from *Laminaria hyperborea*, alginate VLVG™ derived from *Laminaria hyperborea*, alginate MVM™ derived from *Laminaria hyperborea*, alginate LVM™ derived from *Laminaria hyperborea*, and alginates derived from *Macrocystis pyrifera*.

The alginate of the present invention may be used in the form of an initial solution, prepared by dissolving under homogenous conditions, a commercially available form of alginate powder in a suitable solvent or buffer solvent, preferably water, yielding a solution of salt of the alginate. In case of using a scaffold alginate, this initial solution is then gelated to form the wet hydrogel or freeze-dried to form the sponge. This solution subjected to gelation is referred to as the final alginate solution.

According to a further embodiment, the alginate solution, alginate hydrogel or solid alginate sponge used by the method of the invention may further comprises a cross-linking agent selected from the group consisting of the salts of calcium, copper, aluminum, magnesium, strontium, barium, tin, zinc, chromium, organic cations, poly(amino acids), poly(ethyleneimine), poly(vinylamine), poly(allylamine), and cationic polysaccharides.

In a most preferred embodiment, the alginate sponge, hydrogel; or liquid solution used by the method of invention, may comprise a cross-linker agent selected form the group consisting of calcium chloride ($CaCl_2$), strontium chloride ($SrCl_2$) and calcium gluconate (Ca-Gl).

The cross-linker used in the alginate sponge used in the method of the invention is preferably in the form of a cross-linker solution having a concentration of cross-linker sufficient to provide a cross-linker concentration between about 0.1% to about 0.5% w/v in the final solution from which the sponge or liquid alginate is obtained.

It should be appreciated that the alginate sponge, hydrogel or liquid solution used by the method of invention may be prepared from an alginate solution with or without the addition of a cross-linker agent.

In one embodiment, the alginate biomaterial used may be any one of a solid alginate sponge or alginate hydrogel. According to this embodiment, the alginate may be characterized by having at least one of: (a) a diameter in the range between 0.1 mm to 100 mm, preferably, 0.1, 0.2, 0.3, 0.4, 0.5, 0.6, 0.7, 0.8, 0.9, 1.0, 10, 20, 30, 40, 50, 60, 70, 80, 90, or 100 mm; (b) an average pore size in the range between 1 nm to 30000 nm or 300 μm, specifically, 1, 2, 3, 4, 5, 6, 7, 8, 9, 10, 20, 30, 40, 50, 60, 70, 80, 90, 100, 150, 200, 300, 400, 500, 600, 700, 800, 900, 1000, 2000, 3000, 4000, 5000, 6000, 7000, 8000, 9000, 10,000, 20,000, or 30,000 nm or 300 μm; (c) volume of between about 0.001 to 0.1 $cm^3$, specifically, 0.001, 0.002, 0.003, 0.004, 0.005, 0.006, 0.007, 0.008, 0.009, 0.02, 0.03, 0.04, 0.05, 0.06, 0.07, 0.08, 0.09 or 0.1 $cm^3$; and (d) a porosity in the range of 10% to 99%, specifically, of 10, 15, 20, 25, 30, 35, 40, 45, 50, 55, 60, 65, 70, 75, 80, 85, 90, 91, 92, 93, 94, 95, 96, 97, 98 or 99%.

The alginate scaffold prepared from the alginate solution with or without the addition of a cross-linker. The final solutions may have concentrations of alginate or alginate and cross-linker in the ranges of from either LVG or MVG 1% w/v without cross linker to either LVG or MVG 1% w/v and Ca-Gl 1% w/v; either LVG or MVG 1% w/v and Ca-Gl 0.2% w/v; either LVG or MVG 1% w/v and $SrCl_2$ 0.15% w/v; or MVG 1% w/v and $CaCl_2$ 0.1% w/v. It should be appreciated that any of the alginate described herein after, may be used.

According to one specific embodiment, the alginate used by the method of the invention is an alginate cross-linked with between about 0.18 to 0.22%, specifically, 0.18, 0.19, 0.20, 0.21 or preferably, 0.22% (w/v) D-gluconic acid (hemi-calcium salt). Such alginate is referred to by the present invention as a macro-pore alginate. More specifically, such alginate may be further characterized by having at least one of: a 5 mm diameter, a volume of 0.04 $cm^3$, a pore size in the range of 1 μm to 100 μm; at least 0.5 mm thickness; and at least 20% porosity, more specifically, 20, 30, 40, 50, 60, 70, 80, 90, 95 or 99% porosity. According to a specifically preferred embodiment, the alginate scaffold used by the method of the invention has a 5 mm diameter; a volume of 0.04 $cm^3$, a pore size in the range of 50 μm to 100 μm; a 2 mm thickness; and 90% porosity. It should be appreciated that such alginate scaffold is referred to by the invention as macro-pore alginate.

According to another specific embodiment, the alginate used by the method of the invention is an alginate cross-linked with 0.05M $CaCl_2$. Such alginate is referred to by the present invention as a nano-pore alginate, or alginate hydrogel. More specifically, such alginate may be further characterized by having at least one of: a pore size in the range of 1 nm to 1000 nm; a 0.5 mm thickness; and 20% porosity, more specifically, 20, 30, 40, 50, 60, 70, 80, 90, 95 or 99% porosity.

In embodiments where alginate sponges or scaffolds are used, by the method of the invention, they are of a highly porous nature that may be readily invaded by cells and/or blood vessels. The morphology and mechanical properties of the sponges allow for a continuous pore structure with a homogenous pore size distribution and optimal interconnections between the pores.

The alginate sponges used by the method of the invention may be of various shapes and sizes, for example, cube shapes, spherical shapes and cylindrical shapes.

According to an alternative preferred embodiment, the alginate used by the methods of the invention may be in a liquid soluble form. Such liquid alginate biomaterial may be either cross linked or non cross-linked.

In one specific embodiment, the alginate solution used may be between about 0.1 to about 4% (w/v) sodium alginate solution, specifically, 0.1, 0.2, 0.3, 0.4, 0.5, 0.6, 0.7, 0.8, 0.9, 1.0, 2.0, 3.0, or 4%, having a molecular weight of between about 1000 to 50000 Dalton, specifically, 1000, 2000, 3000, 4000, 5000, 6000, 7000, 8000, 9000, 10,000, 20,000, 30,000, 40,000, or 50,000 Dalton. The alginate solution may be cross linked with between about 0.18 to about 0.5% (w/v) calcium gluconate solution (D-gluconic acid, hemi-calcium salt), specifically, an one of 0.18, 0.19, 0.2, 0.3, 0.4, 0.5% (w/v) calcium gluconate solution.

In yet another alternative embodiment, the alginate used by the method of the invention may be a non-cross linked alginate solution. More specifically, such solution may comprise between about 0.1 to about 5% (w/v) sodium alginate solution, specifically, any one of 0.1, 0.2, 0.3, 0.4, 0.5, 0.6, 0.7, 0.8, 0.9, 1, 2, 3, or 5% (w/v) sodium alginate solution. The non-cross-linked alginate solution of the invention may be characterized by having at least one of: molecular weight of between about 1 to about 300, specifically, 1, 2, 3, 4, 5, 6, 7, 8, 9, 10, 20, 30, 40, 50, 60, 70, 80, 90, 100, 200, or 300 kDa and a G/M ratio of between about 0.5 to about 4, specifically, 0.5, 0.6, 0.7, 0.8, 0.9, 1, 2, 3 or 4.

According to this particular embodiment, any of the alginate biomaterials used by the method of the invention may be modified or decorated to improve its binding properties to cells and proteins, preferably by attaching at least one of a cell adhesion promoting peptide and a sulfate group. It should be appreciated that any adhesion promoting peptides, for example, an RGD peptide. According to one specific embodiment, the alginate used by the method of the invention may be particularly a macro-pore alginate scaffold attached or decorated by the RGD peptide, as denoted by SEQ ID NO. 1. Such modified alginate is described in Example 4. In yet another embodiment, the hydrogel alginate may be decorated with the RGD peptide. Still further, the method of the invention may use a modified liquid cross-linked or non-cross linked alginate solution, decorated with RGD peptide of SEQ ID NO. 1. It should be further noted that addition of a sulfate group in order to improve attachment to proteins, is well described by part of the present inventors [see reference: Freeman, I. et al., Biomaterials, 29 (22):3260-3268 (2008); Cohen, S. et al., U.S. patent application Ser. No. 11/649,844, a CIP of U.S. patent application Ser. No. 11/374,279 (2007)].

As indicated in Examples 5 and 6, 200 µl of liquid non-linked alginate solution was used. It should further be appreciated that these preferred amounts of active ingredients used by the present invention are specific for a specific damaged tissue and organ, i.e. the liver. Appropriate concentrations for any other tissue or organ should be determined by the treating physician using experimental assays.

Experimental assays may include in vitro and in vivo experiments, based on the use of animal models, as presented in the invention.

Various growth factors can be used as additional agents by the method of the invention, for example angiogenesis stimulating factors and revascularization enhancing factors.

Thus in a further embodiment, the alginate biomaterials used by the method of invention, optionally comprises at least one angiogenic factor selected from the group consisting of: angiopoietins, metalloproteinase (MMP), fibroblast growth factor (FGF), delta like ligand 4 (Dll4), hepatocyte growth factor (HGF) and vascular endothelial growth factor (VEGF).

These growth factors and angiogenic factors can be encapsulated in biodegradable microparticles or nanoparticles which allow for slow-release or controlled-release and may be embedded into the alginate sponge scaffold. Alternatively, these growth and angiogenic factors may be inserted by conjugation with alginate sulfate as previously described [Freeman, I. et al., Biomaterials, 29 (22):3260-3268 (2008); Cohen, S. et al., U.S. patent application Ser. No. 11/649,844, CIP of U.S. patent application Ser. No. 11/374,279 (2007)].

In another aspect, the invention provides a method for sustaining serum albumin levels and/or lowering the levels of any one of serum ALT and AST levels in a subject suffering of hepatic disorder. The method of the invention comprises the step of administering, preferably in a systemic manner, to said subject, a therapeutically effective amount of at least one biocompatible alginate biomaterial, any modification thereof and any combination thereof.

It should be noted that as used herein, sustaining albumin levels, is meant sustaining or keeping normal albumin levels that are levels comparable to non-diseased or healthy controls. Lowering The ALT or AST levels is meant reducing the levels of ALT or AST I about 2, 3, 4, 5, 6, 7, 8, 9, 10, 100, 200, 300, 400, 500, 600, 700, 800, 900 or 1000 folds, as compared to an appropriate untreated control. Alternatively, reduction in the levels of ALT or AST may be a reduction of least 5%, at least 10%, at least 15%, at least 20%, at least 25%, at least 30%, at least 40%, at least 50%, 60%, 70%, 80%, 90% or even by at least 99 or 100% as compared to the levels of appropriate controls.

In yet another aspect, the invention method for reducing the level of apoptosis, in a damaged liver tissue of a subject suffering of hepatic disorder. The invention further provides a method for increasing cell proliferation in a damaged liver tissue of a subject suffering of hepatic disorder. The method of the invention comprises the step of administering, preferably by a systemic manner, to the treated subject, a therapeutically effective amount of at least one biocompatible alginate biomaterial, any modification thereof and any combination thereof.

It should be appreciated that reduction of the level of apoptosis may be a reduction of least 5%, at least 10%, at least 15%, at least 20%, at least 25%, at least 30%, at least 40%, at least 50%, 60%, 70%, 80%, 90% or even by at least 99 or 100% as compared to the levels of appropriate controls. Elevation of cell proliferation may be by at least 5%, at least 10%, at least 15%, at least 20%, at least 25%, at least 30%, at least 40%, at least 50%, 60%, 70%, 80%, 90% or even by at least 99 or 100% as compared to the levels of appropriate controls.

According to a specifically preferred embodiment, any of the methods of the invention may be specifically suitable for the treatment of a mammalian subject. "Mammal" or "mammalian" for purposes of treatment refers to any animal classified as a mammal including, human, research animals, domestic and farm animals, and zoo, sports, or pet animals, such as dogs, horses, cats, cows, etc. In a particular embodiment said mammalian subject is a human subject.

According to another specific embodiment, the methods of the invention may be applied to a subject suffering from impaired liver function resulting from fulminant hepatic failure, liver disease and/or hepatectomy.

As used herein, the term "fulminant" refers to any event or process that occurs suddenly, quickly and is intense and severe to the point of lethality. A "disease" is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein.

"Fulminant hepatic failure" (FHF) is usually defined as the severe impairment of hepatic functions in the absence of preexisting liver disease. This form of liver failure may result in the development of hepatic encephalopathy (confusion, stupor and coma) and decreased production of proteins (such as albumin and blood clotting proteins) within four weeks of the first symptoms (such as jaundice) of a liver problem.

"Liver disease" includes any conditions that affects the functioning of the liver and include malignant and chronic liver disease.

"Malignant liver disease" includes primary and secondary liver tumors such as heptocellular carcinoma also named hepatoma, cholangio-carcinoma, hepatoblastoma, angiosarcoma of the liver, Kupper cell sarcoma and the malignant metastases of other tumors.

"Chronic liver disease" is a liver disease of slow and persisting process over a long period, the onset of which is insidious, followed by progressive deterioration and destruction of the liver.

Examples of chronic liver diseases include cirrhosis of the liver, alcoholic liver disease, chronic hepatitis C, chronic hepatitis B, fatty liver disease, autoimmune hepatitis, portal hypertension, hemochromatosis, Wilson's disease, Gaucher disease, primary biliary cirrhosis, primary sclerosing cholangitis, sarcoidosis, biliary atresia and Zellweger syndrome.

In yet another aspect, the invention provides at least one biocompatible alginate biomaterial, any modification thereof and any combination thereof for use in the treatment of hepatic disorders.

In a specifically preferred embodiment, any of the biocompatible alginate biomaterial, any modification thereof and any combination thereof are as defined by the invention. Still further, these compositions are specifically applicable for treating impaired liver function resulting from fulminant hepatic failure, liver disease and/or hepatectomy.

According to another aspect, the invention further provides alginate derivatives. More specifically, according to one particular embodiment, the invention relates to a macro-pore alginate scaffold attached or decorated by the RGD peptide, as denoted by SEQ ID NO. 1. Such modified alginate is described in Example 4.

In a further aspect, the invention provides a composition comprising the alginate derivatives or the liquid non-cross-linked alginate of the invention.

Still further, the invention provides therapeutic compositions for the treatment of hepatic disorders. Such composition optionally further comprises pharmaceutically acceptable carrier, diluent, excipient and/or additive.

A further aspect of the invention relates to the use of at least one biocompatible alginate biomaterial, any modification thereof and any combination thereof for the preparation of a pharmaceutical composition for the treatment of hepatic disorders in a subject in need thereof.

According to one specific embodiment, the use of the invention may be specifically effective in repairing and/or regenerating damaged tissue in a liver of a subject suffering from hepatic disorder.

According to one embodiment, the alginate biomaterial used by the invention may be an alginate polysaccharide characterized by having at least one of: (a) a mannuronic acid (M) residue content in the range of between about 0% and about 100% of total residues, between about 10, 15, 20, 25, 30, 35, 40, 45, 50, 55, 60, 65, 70, 75, 80, 85, 90, 95, 100, preferably between about 25% to 65%; (b) a guluronic acid (G) residue content in the range of between about 0% and about 100% of total residues, between about 10, 15, 20, 25, 30, 35, 40, 45, 50, 55, 60, 65, 70, 75, 80, 85, 90, 95, 100, preferably between about 35% to 75%; and (c) a molecular weight between about 1000 to 300,000 Dalton, preferably, between about 1000, 10,000, 15,000, 20,000, 25,000, 30,000, 35,000, 40,000, 45,000, 50,000, 60,000, 70,000, 80,000, 90,000, 100,000, 150,000, 200,000, 250,000, 300,000 Dalton. For injectable liquid alginate solution, preferred molecular weight may range between about 1000 to about below 50,000 Dalton. Hydrogel or sponges may preferably be characterized by having a molecular weight ranging between about 5000 to about 100,000 Dalton.

In a preferred embodiment, the present invention relates to the use of an alginate derived from brown sea algae selected from the group consisting of alginate MVG™ (MVG) derived from *Laminaria hyperborea*, alginate LVG™ derived from *Laminaria hyperborea*, alginate VLVG™ derived from *Laminaria hyperborea*, alginate MVM™ derived from *Laminaria hyperborea*, alginate LVM™ derived from *Laminaria hyperborea*, and alginates derived from *Macrocystis pyrifera*.

According to one embodiment, the alginate used by the invention may be in the form of any one of alginate solution, alginate hydrogel and solid alginate sponge.

According to a further embodiment, the present invention relates to the use of cross linked alginate solution, alginate hydrogel or solid alginate sponge. According to this embodiment, such alginate may further comprises a cross-linking agent selected from the group consisting of the salts of calcium, copper, aluminum, magnesium, strontium, barium, tin, zinc, chromium, organic cations, poly(amino acids), poly (ethyleneimine), poly(vinylamine), poly(allylamine), and cationic polysaccharides.

In a most preferred embodiment, the present invention relates to the use of an alginate comprising a cross-linker agent selected form the group consisting of calcium chloride ($CaCl_2$), strontium chloride ($SrCl_2$) and calcium gluconate (Ca-Gl).

In yet another embodiment, use by the invention may be any one of a solid alginate sponge or alginate hydrogel characterized by having at least one of: (a) a diameter in the range between 0.1 mm to 100 mm; (b) an average pore size in the range between 1 nm to 300 µm; (c) volume of between about 0.001 to 0.1 $cm^3$; and (d) a porosity in the range of 10% to 99%. Specifically, as described herein before.

According to one specific embodiment, the alginate used by the invention is an alginate cross-linked with between about 0.18 to 0.22%, specifically, 0.22% (w/v) D-gluconic acid (hemi-calcium salt). The resulting alginate is referred to by the present invention as a macro-porous alginate. More specifically, such alginate may be further characterized by having at least one of: a 5 mm diameter, a volume of 0.04 $cm^3$, a pore size in the range of 1 µm to 100 µm; at least 0.5 mm thickness; and at least 20% porosity, preferably, as described herein above.

According to another specific embodiment, the alginate used by the invention is a hydrogel alginate cross-linked with 0.05M $CaCl_2$. Such alginate is referred to by the present invention as a nano-porous alginate. More specifically, such alginate may be further characterized by having at least one of: a pore size in the range of 1 nm to 1000 nm; a 0.5 mm thickness; and 20% porosity.

In yet another preferred embodiment, the present invention relates to the use of an alginate sponge o hydrogel, with a continuous pore structure.

According to an alternative preferred embodiment, the alginate used by the invention may be in a liquid soluble form. Such liquid alginate biomaterial may be either cross linked or non cross-linked.

In one specific embodiment, the cross-linked alginate solution used may be between about 0.1 to about 4% (w/v) sodium alginate solution, specifically, 0.1, 0.2, 0.3, 0.4, 0.5, 0.6, 0.7, 0.8, 0.9. 1.0, 2.0, 3.0, or 4%, having a molecular weight of between about 1000 to 50000 Dalton, specifically, 1000, 2000, 3000, 4000, 5000, 6000, 7000, 8000, 9000, 10,000, 20,000, 30,000, 40,000, or 50,000 Dalton. The alginate solution may be cross linked with between about 0.18 to about 0.5% (w/v) calcium gluconate solution (D-gluconic acid, hemi-calcium salt), specifically, an one of 0.18, 0.19, 0.2, 0.3, 0.4, 0.5% (w/v) calcium gluconate solution.

In yet another alternative embodiment, the alginate used by the invention may be a non-cross linked alginate solution. More specifically, such solution may comprise between about 0.1 to about 5% (w/v) sodium alginate solution, specifically, any one of 0.1, 0.2, 0.3, 0.4, 0.5, 0.6, 0.7, 0.8, 0.9, 1, 2, 3, or 5% (w/v) sodium alginate solution. The non-cross-linked alginate solution of the invention may be characterized by having at least one of: molecular weight of between about 1 to about 300, specifically, 1, 2, 3, 4, 5, 6, 7, 8, 9, 10, 20, 30, 40, 50, 60, 70, 80, 90, 100, 200, or 300 kDa and a G/M ratio of between about 0.5 to about 4, specifically, 0.5, 0.6, 0.7, 0.8, 0.9, 1, 2, 3 or 4.

According to this particular embodiment, any of the alginates biomaterials used by the invention may be modified or decorated to improve its binding properties to cells and proteins, preferably by attaching at least one of a cell adhesion promoting peptide and a sulfate group. It should be appreciated that any adhesion promoting peptides, for example, an RGD peptide. According to one specific embodiment, the alginate used by the method of the invention may be particularly a macro-pore alginate scaffold attached or decorated by the RGD peptide, as denoted by SEQ ID NO. 1. Such modified alginate is described in Example 4. In yet another embodiment, the hydrogel alginate may be decorated with the RGD peptide. Still further, the method of the invention may use a modified liquid cross-linked or non-cross linked alginate solution, decorated with RGD peptide of SEQ ID NO. 1. It should be further noted that addition of a sulfate group in order to improve attachment to proteins, is well described by part of the present inventors [see reference: Freeman, I. et al., Biomaterials, 29 (22):3260-3268 (2008); Cohen, S. et al., U.S. patent application Ser. No. 11/649,844, CIP of U.S. patent application Ser. No. 11/374,279].

Optionally, the alginate scaffold used by the method of invention, comprises at least one angiogenic factor selected from the group consisting of: angiopoietins, metalloproteinase (MMP), fibroblast growth factor (FGF), delta like ligand 4 (Dll4), hepatocyte growth factor (HGF) and vascular endothelial growth factor (VEGF).

According to a particularly preferred embodiment, the method of the invention is specifically suitable for the treatment of a mammalian subject. In a particular embodiment said mammalian subject is a human subject.

In one embodiment, the present invention relates to the use of the alginate sponge, hydrogel or solution in a subject suffering from impaired liver function aspect resulting from hepatic failure, liver disease and/or hepatectomy.

In another embodiment of this aspect, the present invention relates to the use of the sponge, hydrogel or alginate solutions in repair of damaged resulting from malignant liver disease such as primary and secondary liver tumors (including heptocellular harcinoma also named hepatoma, cholangiocarcinoma, hepatoblastoma, angiosarcoma of the liver, Kupper cell sarcoma, and the malignant metastases of other tumors) as well as from chronic liver disease such as cirrhosis of the liver, alcoholic liver disease, chronic hepatitis C, chronic hepatitis B, fatty liver disease, autoimmune hepatitis, portal hypertension, hemochromatosis, Wilson's disease, Gaucher disease, primary biliary cirrhosis, primary sclerosing cholangitis, sarcoidosis, biliary atresia and Zellweger syndrome.

The terms "treat, treating, treatment" as used herein and in the claims mean ameliorating one or more clinical indicia of disease activity in a patient having hepatic disease.

"Treatment" refers to therapeutic treatment. Those in need of treatment are mammalian subjects suffering from impaired organ function as a result of tissue damage, removal, or dysfunction. By "patient" or "subject in need" is meant any mammal in which implantation of the alginate scaffold is warranted, in order to promote repair and regeneration of damaged organ tissue.

Another aspect of the invention relates to the use of a therapeutically effective amount of a biocompatible alginate biomaterial, any modification thereof and any combination thereof, for the preparation of a pharmaceutical composition for sustaining normal serum albumin levels in a subject suffering of hepatic disorder.

The invention further provides the use of a therapeutically effective amount of a biocompatible alginate biomaterial, any modification thereof and any combination thereof, for the preparation of a pharmaceutical composition for lowering the levels of any one of serum ALT and AST levels in a subject suffering of hepatic disorder.

In a further aspect, the invention relates to the use of a therapeutically effective amount of a biocompatible alginate biomaterial, any modification thereof and any combination thereof, for the preparation of a pharmaceutical composition for reducing the level of apoptosis in a damaged liver tissue of a subject suffering of hepatic disorder.

The invention further relates to the use of a therapeutically effective amount of a biocompatible alginate biomaterial, any modification thereof and any combination thereof, for the preparation of a pharmaceutical composition for increasing cell proliferation in a damaged liver tissue of a subject suffering of hepatic disorder.

According to one preferred embodiment, the composition of the invention may be administered either systemically or locally. It should be noted that a systemic administration is preferred.

The terms "effective amount" or "sufficient amount" mean an amount necessary to achieve a selected result. The "effective treatment amount" is determined by the severity of the disease in conjunction with the preventive or therapeutic objectives, the route of administration and the patient's general condition (age, sex, weight and other considerations known to the attending physician). Although the method of the invention is particularly intended for the treatment hepatic disorders in mammals, particularly humans, other mammals are also included. By way of non-limiting examples, mammalian subjects include monkeys, equines, cattle, canines, felines, rodents such as mice and rats, and pigs. It should be appreciated that the effective amount may be defined also according to the size and nature of the treated animal.

It should be further noted that for the method of treatment provided in the present invention, said therapeutic effective amount, or dosage, is dependent on severity and responsiveness of the disease state to be treated, with the course of treatment lasting from several days to several weeks, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, or monthly. Persons of ordinary skill in the art can easily estimate repetition rates for dosing based on measured residence times and concentrations of the combined composition of the invention in bodily fluids or tissues. Following successful treatment, it may be optional to have the patient undergo maintenance therapy to prevent the recurrence of the disease state, wherein the combined composition of the invention is administered in maintenance doses, once or more daily.

According to a non-limiting example, effective amount of alginate biomaterial may range between about 1 ng to 100 gr. Preferably, between about 1 mg to about 10 gr, more preferably, 1 mg to 100 mg.

Example 6 clearly presents, using the ConA induced hepatitis model, the applicability of liquid non-cross-linked alginate injected i.p., in treating immune-mediated hepatitis. The possibility of systemically applying alginate solution demonstrates herein for the first time, the feasibility of using alginate for treating any liver damage that may be caused by any immune viral or chemical agent. For example, treatment of liver damage caused by the use of pain killers, such as acetaminophen (Tylenol, for example).

A further aspect of the invention relates to a kit for the preparation of an alginate biomaterial; used by the method of the invention, said kit comprising a suitable alginate polymer, a suitable buffer solvent, optionally a cross linker agent, preferably Ca-Gl, means for implanting into the organ tissue an alginate sponge, hydrogel or solution (either non-cross-linked or cross-linked) prepared from the previous and a manual with instructions on how to prepare the alginate scaffold and instructions of use.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Animals and Surgical Procedures

Male C57BL/6 mice, weighing 25-28 g, were used in all experiments and maintained in a temperature-controlled room with alternating 12-h light/dark cycles. A standard two-third hepatectomy comprised removal of the lateral left, medial left, and medial right lobes. To employ 87% hepatectomy the inventors further resected the lateral, the quadrate lobe and the pyriform process of the liver sparing only the caudate lobe. This procedure provides a model for acute liver failure. All experiments were approved by the Institutional Animal Care and Use Committee of Hadassah University Hospital. Animals received humane care according to the criteria outlined in the *Guide for the Care and Use of Laboratory Animals*.

Macroporous Scaffold Preparation

Macroporous alginate and collagen scaffolds with similar porous structures (90% porosity, 50-100 μm pore size, 0.04 cm$^3$ volume, (FIG. 1), were utilized. The alginate scaffolds (FIG. 1A) were prepared from 1% (w/v) sodium alginate (LVG (100 kDa), 65% G, NovaMatrix, FMC Biopolymer, Drammen, Norway) solution crosslinked with 0.22% (w/v) D-gluconic acid (hemi-calcium salt) by a freeze-dry technique [see Shapiro, L. and Cohen, S. Biomaterials 18 (8):583-90 (1997)]. Calf skin collagen scaffolds (FIG. 1B) were prepared from a 1% (w/v) collagen solution in 0.2% (v/v) acetic acid and then freeze-dried under conditions used for preparing alginate scaffolds. The collagen scaffolds were further subjected to UV cross-linking to enhance stability.

The internal structure of the scaffolds was evaluated by scanning electron microscopy (SEM, Joel JSM-35CF, Tokyo, Japan) after coating thin sections from the scaffold with 100 Å gold, using a polar E5100 coating apparatus.

To detect scaffolds within the liver, macroporous biotin-labeled alginate scaffolds with similar porosity were prepared as described above.

RGD-Modification of Alginate

The peptide GGGGRGDY (BioSight, Karmiel, Israel) also denoted by SEQ ID NO. 1, was covalently-attached to alginate polysaccharide (LVG, 100 kDa, 65% G contents, NovaMatrix FMC Biopolymers, Drammen, Norway) via carbodiimide chemistry [Rowley, J. A. et al. J. Biomed. Mater. Res. 60:217-223 (2002)] to yield a 0.2% rate of modification of uronic acid monomers by the peptide sequences. The macroporous scaffold from RGD-alginate was prepared as described above.

The Effect of Peptide Decoration of Alginate on the Porosity of the Scaffold Fabricated from this Biomaterial The process of alginate scaffold formation [Shapiro, L. and Cohen, S. Biomaterials 18:583-590 (1997)] comprises cross-linking of alginate by bivalent cross-linkers, e.g., calcium gluconate, freezing the cross-linked alginate and lyophilization to produce a sponge-like scaffold. The ionic cross-linking is important to maintain scaffold stability in culture medium, while the freezing process affects pore size and architecture. Scaffold stability and internal morphology are important to address since bulk modification of alginate is done through the covalently bonding of the peptide to the carboxyl group on alginate and as mentioned before, the carboxyl group participates in the alginate cross-linking during scaffold formation.

Evaluation of the scaffold architecture and internal morphology was done by scanning electron microscopy (SEM). The alginate and the RGD-decorated alginate scaffold maintained high porosity with a similar range of pore sizes (55-120 μm in diameter, FIG. 2). The stability of the modified scaffold was tested in culture medium, at 37° C., while mixing or in bioreactor. By visual inspection, the scaffold shape and size did not change for at least 3-weeks.

Preparation of Alginate Hydrogel (Nano-Porous Structure)

The alginate hydrogel was prepared from 1% (w/v) alginate (LVG, 150 kDa, 65% G contents, NovaMatrix, FMC Biopolymer, Drammen, Norway) and was cross-linked with 0.05 M Calcium chloride. This results in the formation of alginate hydrogel with pore size in the range of 1 nm to 1000 nm; a 0.5 mm thickness; and 20% porosity.

Preparation of the Non-Cross Linked Sodium Alginate Solution

Sodium alginate samples (Mw ranging from about 15 to 160 kDa; G/M ratio 2.1) were purchased from FMC Biopolymers, Drammen, Norway. Smaller molecular weight alginate samples were prepared by gamma radiation as described [WO/2008/098109]. For preparation of non-cross-linked solutions: sodium alginate samples were dissolved in double distilled water (DDW) to a final concentration of 1% (w/v). The solution was stirred at room temperature for 24 h for a complete dissolution of the alginate.

Preparation of the Cross Linked Alginate Solution

For preparation of calcium cross-linked solutions: sodium alginate samples were dissolved in double distilled water (DDW) to a final concentration of 2% (w/v) then mixed with 2% (w/v) calcium gluconate solution (D-gluconic acid, hemi-calcium salt, Sigma). The final preferred composition is 1% (w/v) alginate and 0.3% calcium gluconate. The mixtures were homogenized using Heidolph DIAX 900 homogenizer equipped with 10 G head, operating at 26,000 rpm for about 2 minutes. Following homogenization, the preparations were refrigerated at about 4-8° C. until used.

H&E Staining

Hematoxylin-eosin (H&E) staining was used to evaluate liver injury from formalin-fixed and paraffin embedded liver tissue.

BrdU and Caspase-3 Immunohistochemical Staining

Sections from formalin-fixed and paraffin-embedded liver tissue were stained with mouse monoclonal anti-BrdU antibody or mouse antibody raised against activated cleaved) caspase-3.

BrdU incorporation was determined by counting positively stained hepatocyte nuclei in three to six low-power (10×) microscope fields, and the mean was calculated.

Activated caspase-3 labeling was evaluated by counting apoptotic cells in ten low power (40×) microscope fields.

Immunoblot Analysis

For analysis of whole tissue lysates, snap-frozen liver pieces were homogenized in 0.75 ml of ice-cold PBS and then centrifuged at 4° C. for five min in 2000 rpm. Supernatants were discarded and pellets were lysed with 50 mM beta glycerophosphate, 1.5 mM EGTA, pH 7.3, 1 mM EDTA, PH 7.3, 1 mM DTT, 0.1 mM Sodium vanadate, 1% NP-40, and cocktails of protease and phosphatase (Sigma) and then left on ice for 10 min. Lysates were centrifuged at 4° C. for 10 minutes in 14000 rpm and sup was moved to clean tubes. Equivalent amounts of lysates (15 μg/lane), determined by Bradford assay (Bio-Rad, Rehovot, Israel), were separated by sodium dodecyl sulfate polyacrylamide gel electrophoresis (SDS-PAGE) and transferred to nitrocellulose membranes. Proteins were detected using anti-STAT-3 or anti-phosphorylated STAT3-Ser727 antibodies (Cell Signaling Technologies, MA).

Liver Enzymes and Albumin

Sera from individual mice were obtained. Serum AST, ALT and albumin levels were measured by an automatic analyzer.

Statistical Analysis

Quantitative data were expressed as mean±SEM. If standard deviations (SD) were equal within the populations, an unpaired two-tailed Student t test was used to compare treatment groups. Kaplan-Meir survival curve was done to assess survival with log rank test for significance. p values lower that 0.05 were considered significant.

Experimental Groups

Figure 1A:
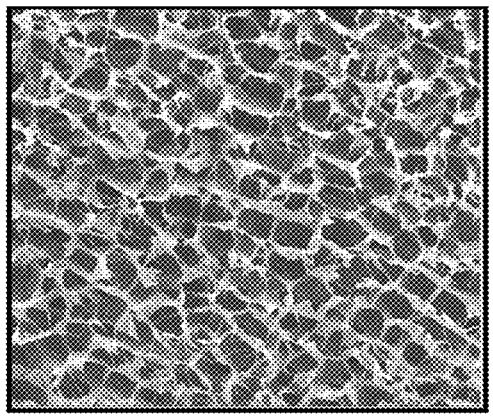
FIG. 1A-1B: Alginate structure
Figure 1B:
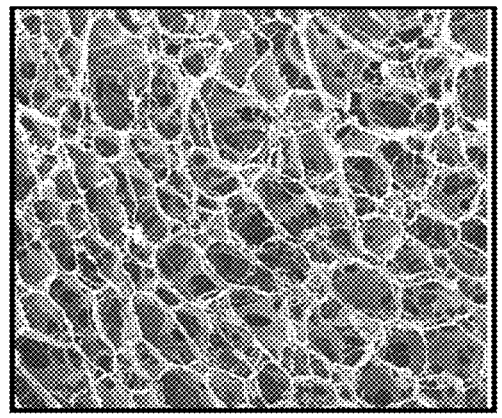

Two sets of experiments were conducted. In a first set, the feasibility of a macroporous alginate scaffold to enhance liver reconstruction after partial hepatectomy (PH) was examined and compared to macroporous collagen scaffold. As shown by FIGS. 1A and 1B both Alginate and collagen scaffolds had similar porous structure (FIGS. 1A and 1B, respectively), and differ by their chemical nature. The collagen scaffold is frequently used in surgeries for hemostasis and was used by the inventors as control to assess whether the effect of the alginate scaffold is by hemostasis.

The second experimental set examined the efficiency of macroporous alginate scaffold in reducing liver cell death following PH as compared to alginate hydrogel having a nano-porous structure and a modified alginate, specifically, RGD-decorated alginate macroporous scaffold.

Three scaffolds per animal were positioned on the liver remnant after hepatectomy. To assess animal survival, the treated and sham-operated groups, 10 mice in each, were followed for 6 days without harvesting any specimens. To analyze liver and serum, mice were scarified at 3, 6, 24, 48 hours and 6 days after hepatectomy, 3-5 mice in each group.

Liquid non-cross-linked alginate biomaterial solution was examined using two experimental models, the partial extensive hepatectomy and the ConA induced immune-mediated hepatitis. Experimental groups of both models are described in details by Examples 5 and 6.

Example 1

Survival Among the Experimental Groups

Hepatectomy is often the last and best resort for large hepatic tumors and metastasis. However, hepatectomy may severely impair hepatic functions and thereby survival of patients under conditions were surgical resection of the liver is warranted. As shown in FIG. 3, survival was significantly higher in the group with the implanted alginate scaffold, 60% vs. 10% without the scaffold (log rank=0.001). There was no significant difference in survival in the collagen and no-scaffold groups, indicating that the effect of the alginate scaffold is not mediated through hemostasis. Survival significantly decreased when either a collagen scaffold or no scaffold were used. The inventors further valuated the hepatocellular damage in the three experimental groups, as demonstrated by FIG. 4. As shown by the figure, three hours after hepatectomy, massive necrosis is clearly apparent in the control group whereas the alginate group demonstrates almost normal liver architecture. As time progress after hepatectomy, inflammatory cells are seen in the parenchyma and fibrosis is prominent.

Example 2

Liver Enzymes and Albumin Levels Among Experimental Groups

Liver transaminase provides evidence for hepatic cell injury, whereas albumin provides indication for the synthetic ability of the liver. Testing gives an indication about the state of a patient's liver. As shown in FIGS. 5A, 5B and Table 1, ALT and AST levels confirmed the histopathological findings demonstrating significantly increase of between two to twenty folds in the control groups versus nearly normal levels in mice with the implanted alginate scaffold ($p<0.0001$ in 6, 24, hours and 6 days). Levels peaked 24 hours after hepatectomy in groups without scaffold and collagen scaffold and remain stable in the alginate group.

As shown by FIG. 6, albumin was significantly higher in the alginate group versus the collagen group and the control. These results indicated that alginate scaffold prevents hepatocellular damage and improves hepatic synthetic function after subtotal partial hepatectomy.

TABLE 1

Summary of AST, ALT and albumin levels

| Time | Scaffold | AST (mean ± S.D) | ALT (mean ± S.D) | Albumin (mean ± S.D) | p value* | p value** |
|---|---|---|---|---|---|---|
| 6 hours | Alginate | 186 ± 35 | 160 ± 46 | 25 ± 5.8 | 0.0002 | 0.01 |
|  | Collagen | 745 ± 8 | 722 ± 246 | 12 ± 4.6 |  |  |
|  | No-scaffold | 750 ± 0 | 898 ± 89 | 10 ± 0.5 |  |  |
| 24 hours | Alginate | 113 ± 34 | 94 ± 45 | 26 ± 1.7 | 0.0002 | 0.00008 |
|  | Collagen | 2180 ± 432 | 1239 ± 238 | 11 ± 1.7 |  |  |
|  | No-scaffold | 1269 ± 401 | 1316 ± 158 | 10 ± 0 |  |  |

TABLE 1-continued

Summary of AST, ALT and albumin levels

| Time | Scaffold | AST (mean ± S.D) | ALT (mean ± S.D) | Albumin (mean ± S.D) | p value* | p value** |
|---|---|---|---|---|---|---|
| 6 days | Alginate | 122 ± 42 | 86 ± 29 | 24 ± 1.5 | 0.002 | 0.0001 |
| | Collagen | 712 ± 393 | 641 ± 335 | 10 ± 0 | | |
| | No-scaffold | 748 ± 429 | 595 ± 306 | 10 ± 0 | | |

*p value comparing ALT values between alginate and no scaffold
**p value comparing albumin levels between alginate and collagen Example 3

Effect of Alginate on Apoptosis and Cell Replication

To further investigate whether the beneficial effect of application of alginate on the remaining liver tissue involved apoptotic processes, the inventors next compared apoptotic markers in the three experimental groups. As shown by FIG. 7, immuno-histochemistry for cleaved caspase 3 was significantly higher in the control groups, while in the alginate-treated group no staining noted, suggesting a significantly reduced apoptosis in the alginate treated group. The absent of caspase 3 staining in the alginate group is particularly meaningful in view of the marked increase in apoptosis in the control groups, especially 24 hours after hepatectomy.

The inventors therefore next examined the effect of alginate treatment on cell replication. BrdU was used as a marker for hepatocyte replication. As shown by FIG. 8, a significant increase in cell staining is clearly demonstrated at 3, 6 and 24 hours in the alginate treated group. It should be noted that only after 48 hours, an increase in hepatocyte replication could be detected in all experimental groups. These results indicate that alginate scaffolds improve regeneration early after partial hepatectomy and the second increase in replication is independent of Alginate.

To further analyze the signaling pathways mediating the observed increase of cell proliferation in response to alginate treatment, STAT3 activation was next examined. As shown by FIG. 9, immunoblot for STAT3 and Phospho STAT3 clearly demonstrates an increase in STAT3 activation 6 and 24 hours after PH in the alginate group versus the control groups. Without being bound by any theory, these results suggest that alginate may increase survival by promoting activation of STAT-3 thereby initiating an intensive regenerative response.

Example 4

Modified Alginates in the Treatment of Hepatectomy

Encouraged by the results using the macroporous alginate scaffold, the inventors next tested the effect of different modified alginates preparations. Therefore, survival of hepatectomized mice treated with either, nano-pore alginate hydrogel, macro-pore alginate scaffold, macro-pore collagen scaffold or untreated control was next examined. As shown by FIG. 10, both nano-pore and macro-pore alginate scaffolds significantly elevated mice survival, particularly as compared to collagen scaffold or untreated control groups. Further analysis presented by FIG. 11, demonstrates comparable enhanced survival of mice treated with nano-pore alginate scaffold (alginate hydrogel).

Further analysis of modified alginates, for example, RGD-decorated alginate scaffold presented by FIGS. 12 and 13, showed comparable effects on transaminases (AST in FIG. 12A, ALT in FIG. 12B) and albumin (FIG. 13).

Biotin-labeled alginate was next used as a tool for assessing the in vivo position of the scaffold. Therefore, biotin-alginate scaffolds were created and inserted after hepatectomy and mice were scarified at 3 and 6 hours after surgery. As shown by the immunohistochemical H&E staining presented by FIG. 14, biotin was detected within the liver tissue suggesting the liver regenerated on the scaffolds.

Example 5

Use of Non-Cross Linked Liquid Alginate in the Treatment of Hepatectomy

The remarkable results of applying different alginate scaffolds on damaged hepatic tissue, led the present inventors to further evaluate the feasibility of using different applications of alginate on the injured tissue, specifically, in a liquid form. Therefore, extended (87%) partial hepatectomy was preformed in two groups of mice (10 mice per group) as described above, and the effect of liquid alginate on mice survival was compared to PBS control. Liquid alginate (200 μl) or PBS, were sprayed on top of the liver remnant after the hepatectomy without injecting into the liver parenchyma. As clearly shown by FIG. 15, after 100 hours 80% of mice treated with liquid alginate survived, whereas only 40% of PBS treated mice survived. After 144 hours, all control PBS treated mice died whereas 60% of liquid alginate treated mice survived. After 10 days all mice died.

The effect of liquid alginate on the recovery of hepatectomized liver tissue was further assessed by examining functional parameters. Thus, serum ALT levels were measured in mice treated with liquid alginate or PBS (n=4), at 6 and 24 hours after extensive hepatectomy. Serum was obtained from the tail vein at 6 hours. Both serum and liver were isolated 24 hours after PH from sacrificed mice. FIG. 16A depicts that serum ALT levels were significantly elevated in the PBS treated group vs. the liquid alginate group at 6 and 24 hours post extensive PH (p=0.000001 and p=0.000001, respectively). Furthermore, ALT levels significantly decreased from 6 to 24 hours in the liquid alginate treated group (p=0.01).

To assess the hepatic synthetic functions, serum albumin was measured 24 hours after extensive PH. As demonstrated by FIG. 16B, liquid alginate treated mice showed significant elevated levels of serum albumin as compared to PBS treated controls (p=0.000001).

These results clearly demonstrate the feasibility of using alginate either by liquid or solid scaffold forms for recovering injured liver tissue.

Example 6

The Effect of Liquid Non-Cross Linked Alginate on ConA Induced Hepatitis

Concanavalin A (Con A) is a widely used model for immune mediated liver injury. Con A induces acute immune-mediated liver injury upon a single intravenous injection to mice. To study the effect of injectable liquid alginate on the hepatic injury, 200 μl of ConA (400 μg/mouse=20 mg/kg) were injected to mice tail vein (n=4) two hours after IP injection of either 200 μl of liquid alginate or PBS. Serum was obtained from tail vein for analysis of ALT levels at 6 and 24 after ConA injection. Mice were sacrificed at 48 hours after ConA injection, and serum (for ALT and albumin) and liver were obtained. FIG. 17A depict a significant lower levels of serum ALT 6 and 24 hours after ConA injection in the alginate treated group vs. the control group (p=0.004 and 0.04, respectively). Forty eight hours after ConA injection, the ALT levels were two folds higher in the control group as compared to the liquid alginate-treated group, however, this has not reached a statistical significance.

To assess the hepatic synthetic function serum albumin was measured 48 hours after ConA injection. As shown by FIG. 17B, the levels of serum albumin was significantly higher in the liquid alginate treated mice (p=0.00000001).

These results clearly demonstrate the feasibility of using liquid alginate biomaterial for suppressing hepatic inflammation, improving survival and hepatic synthetic functions in the two different acute liver failure models examined herein, the extensive partial hepatectomy as well as in immune hepatitis (ConA).

about 0.18 to 0.22% (w/v) D-gluconic acid (hemi-calcium salt), and having at least one of: a 5 mm diameter, a volume of 0.04 cm$^3$, a pore size in the range of 1 μm to 100 μm; at least 0.5 mm thickness; and at least 20% porosity.

6. The method according to claim 4, wherein said alginate hydrogel is an alginate cross-linked with at least 0.05M CaCl$_2$ and has at least one of: a pore size in the range of 1 nm to 1000 nm; a 0.5 mm thickness; and 20% porosity.

7. The method according to claim 3, wherein said alginate solution comprises between about 0.1 to about 4% (w/v) sodium alginate, the alginate within the solution having a molecular weight of between about 1000 to 50000 Dalton, and being cross linked with between about 0.18 to about 0.5% (w/v) calcium gluconate solution (D-gluconic acid, hemi-calcium salt).

8. The method according to claim 2, wherein said alginate solution comprises between about 0.1 to about 5% (w/v) non-cross-linked sodium alginate having a G/M ratio of between about 0.5 to about 4.

9. The method according to claim 2, wherein said alginate is modified to improve its binding properties to cells and proteins by attaching at least one of a cell adhesion promoting peptide and a sulfate group.

10. A method for sustaining serum albumin levels in a subject suffering impaired liver function resulting from ful-

The invention claimed is:

1. A method for the treatment of impaired liver function in a subject in need thereof, said impaired liver function resulting from fulminant hepatic failure and/or a liver disease selected from the group consisting of autoimmune hepatitis, chronic hepatitis C, and chronic hepatitis B, which method comprises the step of administering to said subject a therapeutically effective amount of at least one biocompatible alginate biomaterial, wherein said alginate has a molecular weight in a range of from 1000 to 300,000 Dalton, and wherein the method does not comprise administering cells.

2. The method according to claim 1, wherein said alginate is in the form of any one of alginate solution, alginate hydrogel and solid alginate sponge.

3. The method according to claim 2, wherein said alginate solution, alginate hydrogel or solid alginate sponge further comprises a cross-linking agent selected from the group consisting of the salts of calcium, copper, aluminum, magnesium, strontium, barium, tin, zinc, chromium, organic cations, poly (amino acids), poly(ethyleneimine), poly(vinylamine), poly (allylamine), and cationic polysaccharides.

4. The method according to claim 3, wherein said alginate is any one of a solid alginate sponge or alginate hydrogel having a porosity in the range of 10% to 99%.

5. The method according to claim 4, wherein said solid alginate sponge is an alginate cross-linked with between minant hepatic failure, hepatectomy and/or a liver disease selected from the group consisting of autoimmune hepatitis, chronic hepatitis C, and chronic hepatitis B, wherein said method comprises the step of systemically administering to said subject a therapeutically effective amount of at least one biocompatible alginate biomaterial, wherein said alginate has a molecular weight in a range of from 1000 to 300,000 Dalton.

11. A method for lowering the levels of any one of serum ALT and AST levels in a subject suffering of impaired liver function resulting from fulminant hepatic failure, hepatectomy and/or a liver disease selected from the group consisting of autoimmune hepatitis, chronic hepatitis C, and chronic hepatitis B, wherein said method comprises the step of systemically administering to said subject a therapeutically effective amount of at least one biocompatible alginate biomaterial, wherein said alginate has a molecular weight in a range of from 1000 to 300,000 Dalton.

12. A method for reducing the level of apoptosis in a damaged liver tissue of a subject suffering of impaired liver function resulting from fulminant hepatic failure, hepatectomy and/or a liver disease selected from the group consisting of autoimmune hepatitis, chronic hepatitis C, and chronic hepatitis B, wherein said method comprises the step of systemically administering to said subject a therapeutically effective amount of at least one biocompatible alginate biomaterial, wherein said alginate has a molecular weight in a range of from 1000 to 300,000 Dalton.

13. A method for increasing cell proliferation in a damaged liver tissue of a subject suffering impaired liver function resulting from fulminant hepatic failure, hepatectomy and/or a liver disease selected from the group consisting of autoimmune hepatitis, chronic hepatitis C, and chronic hepatitis B, wherein said method comprises the step of systemically administering to said subject a therapeutically effective amount of at least one biocompatible alginate biomaterial, wherein said alginate has a molecular weight in a range of from 1000 to 300,000 Dalton.

14. The method according to claim 1, wherein said administration step is performed systemically.

15. A method for the treatment of impaired liver function in a subject in need thereof, said impaired liver function resulting from fulminant hepatic failure, hepatectomy and/or a liver disease selected from the group consisting of autoimmune hepatitis, chronic hepatitis C, and chronic hepatitis B, which method comprises the step of administering to said subject a therapeutically effective amount of at least one biocompatible alginate biomaterial, wherein said alginate has a molecular weight in a range of from 1000 to 300,000 Dalton, and is in a form of an alginate solution comprising between about 0.1 to about 5% (w/v) non-cross-linked sodium alginate.

* * * * *

SEQUENCE LISTING

```
<160> NUMBER OF SEQ ID NOS: 1

<210> SEQ ID NO 1
<211> LENGTH: 8
<212> TYPE: PRT
<213> ORGANISM: artificial
<220> FEATURE:
<223> OTHER INFORMATION: the RGD adhesion peptide

<400> SEQUENCE: 1

Gly Gly Gly Gly Arg Gly Asp Tyr
1               5
```